(12) United States Patent
Yamanaka et al.

(10) Patent No.: US 8,986,989 B2
(45) Date of Patent: Mar. 24, 2015

(54) METHOD FOR PRODUCING USEFUL SUBSTANCES BY A RECOMBINANT ACTINOMYCETE, STREPTOMYCES SPECIES

(75) Inventors: Kazuya Yamanaka, Kanagawa (JP); Yoshimitsu Hamano, Fukui (JP); Tomohiro Yoshimura, Kanagawa (JP)

(73) Assignee: JNC Corporation, Tokyo (JP)

( * ) Notice: Subject to any disclaimer, the term of this patent is extended or adjusted under 35 U.S.C. 154(b) by 49 days.

(21) Appl. No.: 13/581,878

(22) PCT Filed: Mar. 2, 2011

(86) PCT No.: PCT/JP2011/054763
§ 371 (c)(1),
(2), (4) Date: Oct. 18, 2012

(87) PCT Pub. No.: WO2011/108585
PCT Pub. Date: Sep. 9, 2011

(65) Prior Publication Data
US 2013/0052684 A1  Feb. 28, 2013

(30) Foreign Application Priority Data
Mar. 3, 2010 (JP) ................. 2010-046781

(51) Int. Cl.
| | |
|---|---|
| C12N 5/00 | (2006.01) |
| C12N 15/00 | (2006.01) |
| C12P 21/06 | (2006.01) |
| C12P 21/02 | (2006.01) |
| C12N 15/63 | (2006.01) |
| C12N 15/76 | (2006.01) |
| C12P 17/16 | (2006.01) |
| C12P 19/04 | (2006.01) |

(52) U.S. Cl.
CPC ............... *C12N 15/63* (2013.01); *C12N 15/76* (2013.01); *C12P 17/165* (2013.01); *C12P 19/04* (2013.01); *C12P 21/02* (2013.01)
USPC ....... 435/325; 435/320.1; 435/69.1; 435/183; 435/252.3; 435/252.35

(58) Field of Classification Search
None
See application file for complete search history.

(56) References Cited

U.S. PATENT DOCUMENTS

2010/0248305 A1   9/2010 Yamanaka et al.

FOREIGN PATENT DOCUMENTS

JP        2008-263868        11/2008

OTHER PUBLICATIONS

Score Report to SEQ ID No. 4 reference to Yamanaka et al in "Epsilon-poly-L-lysine disparity is controlled by a highly unusual nonribosomal peptide synthetase" (Nature Chemical Biology, 2008,vol. 4, No. 12, pp. 766-772.*
Supplementary European Search Report issued Oct. 16, 2013 in corresponding European Application No. 11 75 0694.
Yamanaka et al., "Supplementary information: ε-poly-L-lysine dispersity is controlled by a highly unusual non-ribosomal peptide synthetase", Nature Chemical Biology, vol. 4, No. 12, Dec. 2008, pp. 1-16.
Yamanaka et al., "Development of a recombinant ε -poly-L-lysine synthetase expression system to perform mutational analysis", Journal of Bioscience and Bioengineering, vol. 111, No. 6, 2011, pp. 646-649.
International Search Report issued Jun. 7, 2011 in corresponding International (PCT) Application No. PCT/JP2011/054763.
Written Opinion issued Jun. 7, 2011 in corresponding International (PCT) Application No. PCT/JP2011/054763.
S. Herai et al., "Hyper-inducible expression system for streptomycetes", PNAS, vol. 101, No. 39, pp. 14031-14035, Sep. 28, 2004.
H. Zhao et al., "Regeneration of cofactors for use in biocatalysis", Current Opinion in Biotechnology, vol. 14, pp. 583-589, 2003.
M. Sato et al., "Thermostable ATP Regeneration System Using Polyphosphate Kinase from *Thermosynechococcus elongatus* BP-1 for D-Amino Acid Dipeptide Synthesis", Journal of Bioscience and Bioengineering, vol. 103, No. 2, pp. 179-184, 2007.
M. Nishikawa et al., "Distribution of Microbes Producing Antimicrobial ε-Poly-$_L$-Lysine Polymers in Soil Mircoflora Determined by a Novel Method", Applied and Environmental Microbiology, vol. 68, No. 7, pp. 3575-3581, Jul. 2002.
J. Hiraki et al., "Improved ε-Poly-$_L$-Lysine Production of an S-(2-Aminoethyl)-$_L$-Cysteine Resistant Mutant of *Streptomyces albulus*", Seibutsu-kogaku Kaishi, vol. 76, No. 12, pp. 487-493, 1998, with partial English translation.
K. Yamanaka et al., "ε-Poly-$_L$-lysine dispersity is controlled by a highly unusual nonribosomal peptide synthetase", Nature Chemical Biology, vol. 4, No. 12, pp. 766-772, Dec. 2008.
Y. Hamano et al., "A highly unusual non-ribosomal peptide synthetase producing an amino-acid homopolymer", Short Review, vol. 54, No. 11, 2009, with English translation.
K. Yamanaka et al., "Epsilon- poly-$_L$-lysine dispersity is controlled by a highly unusual nonribosomal peptide synthetase", Nucleotide, Alphabet of Life, Database GenBank [online], http:// www.ncbi.nlm.nih.gov/nuccore/AB385841, Nov. 19, 2008.
K. Yamanaka et al., "Mechanism of ε-Poly-$_L$-Lysine Production and Accumulation Revealed by Identification and Analysis of an ε-Poly-$_L$-Lysine-Degrading Enzyme", Applied and Environmental Microbiology, vol. 76, No. 17, pp. 5669-5675, 2010.
P. Kahar et al., "Enhancement of ε-Polylysine Production by *Streptomyces albulus* Strain 410 Using pH Control", Journal of Bioscience and Bioengineering, vol. 91, No. 2, pp. 190-194, 2001.
Y. Hamano et al., "Elucidation of ε-Poly-$_L$-Lysine Synthase Reaction Mechanism", Bioscience & Industry, vol. 67, No. 7, pp. 338-341, Jul. 2007, with English translation.

* cited by examiner

*Primary Examiner* — Catherine Hibbert
(74) *Attorney, Agent, or Firm* — Wenderoth, Lind & Ponack, L.L.P.

(57) ABSTRACT

The invention provides a promoter derived from a genome of an actinomycete, *Streptomyces* species, and can specifically induce expression of a transgene in an actinomycete, *Streptomyces* species, in and after a logarithmic growth phase, and an actinomycete host having a high secondary metabolite production ability and a high precursor supply ability in and after the logarithmic growth phase, and a method for producing useful substances in which the promoter and the actinomycete host are combined.

14 Claims, 4 Drawing Sheets

| position | score | predicted promoter sequence |
|---|---|---|
| −343 ∼ −294 | 0.46 | GAAGTCGATGAATATGTGCTCAGTTGCGCAATCATTTAGACAAGGCTTGA (SEQ ID NO: 1) |
| −249 ∼ −200 | 0.68 | TTTTATCGGCACGGGGGAGTGGTGCCGAAAACAATCCCCGGCCCGAGTCA (SEQ ID NO: 2) |
| −231 ∼ −182 | 0.46 | GTGGTGCCGAAAACAATCCCCGGCCCGAGTCAATTCTTTCCCACGCCGTG (SEQ ID NO: 3) |

METHOD FOR PRODUCING USEFUL SUBSTANCES BY A RECOMBINANT ACTINOMYCETE, STREPTOMYCES SPECIES

TECHNICAL FIELD

The invention relates to a method for producing useful substances by a recombinant actinomycete, *Streptomyces* species.

BACKGROUND ART

An actinomycete, *Streptomyces* species, has been widely utilized all over the world as a producer for various useful substances including pharmaceuticals and pharmaceutical intermediates as typified by an antibiotic or an immunosuppressor, and is industrially very useful microorganisms. Even with development of genetic engineering technologies in recent years, a classical method by mutagen treatment is still predominant in breeding a high producer strain for useful substances in the actinomycete including the *Streptomyces* species because not only homologous recombination on the chromosome but also gene transfer and transformation as a vector are currently limited to certain actinomycete strains.

A genome sequence has been determined also in the actinomycete, *Streptomyces* species, in recent years. Therefore, researches are expected to be actively conducted on new physiologically active substances based on genome information in the future. However, for the purpose of developing such substances, linking of genetic information in the genome with production of the useful substances or an enzyme protein that catalyzes synthesis thereof is important, and a host-vector system applicable as a tool is essential.

A gene expression system in microorganisms such as *Escherichia coli* and yeast has been widely spread and commonly utilized. However, proteins that can be expressed as an active form in a common expression system therefor is limited. Similarly, even though an industrially important gene (P-450 or the like) from the actinomycete can be expressed in closely-related *Streptomyces* species, the gene can not be expressed as an active protein or enzyme in the common system therefor in many cases.

Several gene expression systems in the *Streptomyces* species have been developed. In one case, a powerful gene expression system in which large quantities of recombinant proteins as high as 40% of all intracellular soluble proteins can be produced has been reported (Non-patent document 1: Herai et al., Proc Natl Acad Sci USA. 2004 Sep. 28; 101(39): 14031-5. Epub 2004 Sep. 17). However, the systems are provided for the purpose of producing the recombinant proteins. An actinomycete host-vector system that can be applied for producing useful compounds by recombinant microorganisms is virtually unknown. The reason therefor is that achievement of high productivity of a secondary metabolite by using the recombinant microorganisms simultaneously requires specific inducible gene expression during a period suitable for producing the secondary metabolite definitive to the host and also an improvement of precursor supply ability of the host.

Meanwhile, among reactions catalyzed by an organism and a biocatalyst (enzyme) in the organism, reactions catalyzed by ATP-dependent enzymes include many physiologically and also industrially useful reactions. However, ATP is very expensive. Therefore, use of a remarkable amount of ATP as a raw material is quite difficult in industrial production. Thus, many ATP regeneration systems have been reported in which ATP once consumed in the reaction is regenerated by utilizing other energy substances (Non-patent document 2: Zhao & von der Donk, Curr Opin Biotechnol. 2003 December; 14(6): 583-9).

An example has been recently reported in which a thermostable polyphosphate kinase is coexpressed together with an ATP-dependent D-alanine-D-alanine ligase as a dipeptide synthetase in *Escherichia coli* to carry out dipeptide synthesis reaction using the engineered cells, and thus dipeptide synthesis has been achieved with the aid of ATP regeneration system mediated by the polyphosphate kinase. (Non-patent document 3: Sato et al., J Biosci Bioeng. 2007 February; 103(2): 179-84). In the method, the dipeptide synthesis has been achieved at a yield of 80% (mol/mol) as an added D-alanine without adding ATP from outside a system. However, the amount of the product was not so high with a productivity of approximately 0.02 mol/l, indicating that the amount of ATP available for the reaction was approximately 0.02 mol/l.

Several *Streptomyces* species, a certain *Kitasatospora* strain, and a *Epichloe* strain, a filamentous fungi have been reported to extracellularly perform secretory production of ε-poly-L-lysine that is widely utilized as a food preservative in Japan, Republic of Korea and the United States (Non-patent document 4: Nishikawa & Ogawa, Appl Environ Microbiol. 2002 July; 68(7): 3575-81). Among such e-poly-L-lysine producers, *S. albulus* NBRC14147 is particularly industrially useful because the *S. albulus* NBRC14147 shows a remarkably high productivity.

In recent years, an ε-poly-L-lysine synthetase (Pls) and a gene thereof (pls gene) in *S. albulus* have been identified, and ε-poly-L-lysine has been elucidated to be directly synthesized from L-lysine and ATP both as a precursor (Non-patent document 5: Yamanaka et al., Nat Chem Biol. 2008 December; 4(12): 766-72. Epub 2008 Nov. 9, Patent document 1: JP 2008-263868 A). Moreover, a ε-poly-L-lysine high producer mutant has been derived from *S. albulus* wild strain by a mutagen treatment (Non-patent document 6: Hiraki et al., Seibutsu-kogaku Kaishi 76(12) pp. 487-493 1998 12 25; Non-patent document 7: Kahar et al., J Biosci Bioeng. 2001; 91(2): 190-4), and has been actually utilized for industrial production of the ε-poly-L-lysine.

CITATION LIST

Patent Documents

Patent document 1: JP 2008-263868 A.

Non-Patent Documents

Non-patent document 1: Herai et al., Proc Natl Acad Sci USA. 2004 Sep. 28; 101(39): 14031-5. Epub 2004 Sep. 17.

Non-patent document 2: Zhao & von der Donk, Curr Opin Biotechnol. 2003 December; 14(6): 583-9.

Non-patent document 3: Sato et al., J Biosci Bioeng. 2007 February; 103(2): 179-84.

Non-patent document 4: Nishikawa & Ogawa, Appl Environ Microbiol. 2002 July; 68(7): 3575-81.

Non-patent document 5: Yamanaka et al., Nat Chem Biol. 2008 December; 4(12): 766-72. Epub 2008 Nov. 9.

Non-patent document 6: Hiraki et al., Seibutsu-kogaku Kaishi 76(12) pp. 487-493 1998 12 25.

Non-patent document 7: Kahar et al., J Biosci Bioeng. 2001; 91(2): 190-4.

SUMMARY OF INVENTION

Technical Problem

Considering such background, a development has been required for a host-vector system that can regulate specific expression of a transgene in an actinomycete (*Streptomyces* species, for example) having a high substance production ability and precursor supply ability, and can be a tool for researching new physiologically active substances or producing useful physiologically active substances. A development has also been required for a more effective ATP regeneration system that can be applied to mass production of useful substances.

Solution to Problem

Accordingly, the invention provides a promoter, an expression vector, a host cell, and a method for producing desired substances as described below.

Item 1. A promoter capable of specifically inducing gene expression in and after a logarithmic growth phase in an actinomycete, *Streptomyces* species.

Item 2. The promoter according to item 1, wherein the actinomycete, *Streptomyces* species, is an ε-poly-L-lysine producer.

Item 3. The promoter according to item 2, which is present in an approximately 350-bp upstream region of an initiation codon (ATG or GTG) of a pls gene of ε-poly-L-lysine producer.

Item 4. The promoter according to any one of items 1 to 3, comprising the nucleotide sequence of SEQ ID NO: 1, SEQ ID NO: 2, SEQ ID NO: 3 or SEQ ID NO: 4.

Item 5. The promoter according to any one of items 1 to 4, comprising the nucleotide sequence of SEQ ID NO: 4.

Item 6. An expression vector, comprising the promoter according to any one of items 1 to 5.

Item 7. The expression vector according to item 6, for use in expressing an objective gene in an ε-poly-L-lysine producer.

Item 8. The expression vector according to item 7, wherein the ε-poly-L-lysine producer is an actinomycete, *Streptomyces* species, an actinomycete, *Kitasatospora* species, or a filamentous fungus, *Epichloe* species.

Item 9. The expression vector according to item 8, wherein the actinomycete, *Streptomyces* species, is *S. albulus*.

Item 10. The expression vector according to any one of items 6 to 9, further comprising a terminator downstream of the promoter.

Item 11. The expression vector according to item 10, wherein the nucleotide sequence of the terminator includes the nucleotide sequence of SEQ ID NO: 7 or SEQ ID NO: 8.

Item 12. The expression vector according to item 10 or 11, further comprising a tag sequence under regulation of the promoter.

Item 13. The expression vector according to item 12, wherein the tag sequence comprises the nucleotide sequence of SEQ ID NO: 9 or SEQ ID NO: 10.

Item 14. The expression vector according to any one of items 6 to 13, comprising an objective gene under the control of the promoter.

Item 15. The expression vector according to item 14, wherein the objective gene is a gene or a gene cluster derived from an organism of a kind identical with or different from the ε-poly-L-lysine producer.

Item 16. The expression vector according to item 15, wherein the objective gene is a pls gene, a bpsA gene, a hasA gene, a mhasA gene, a hasB gene, a hasB homolog gene, a hasD gene or a hasD homolog gene.

Item 17. An expression vector, comprising the nucleotide sequence of SEQ ID NO: 13, SEQ ID NO: 14 or SEQ ID NO: 15.

Item 18. A host cell, into which the promoter according to any one of items 1 to 5 and an objective gene under regulation of the promoter, or the expression vector according to any one of items 14 to 16 have been transferred.

Item 19. The host cell according to item 18, which is an actinomycete, *Streptomyces* specie, an actinomycete, *Kitasatospora* species, or a filamentous fungus, *Epichloe* species.

Item 20. The host cell according to item 19, which is an ε-poly-L-lysine producer.

Item 21. A method for producing useful substances, comprising expressing an objective gene under regulation of the promoter according to any one of items 1 to 5 to produce a protein or a polypeptide to be encoded by the gene in a host cell.

Item 22. The method according to item 21, comprising transferring the expression vector according to any one of items 14 to 16 into the host cell.

Item 23. A method for producing useful substances, comprising cultivating the host cell according to any one of items 18 to 20.

Item 24. The method for producing useful substances according to item 21, comprising cultivating a pls gene-defective or gene-disrupted strain of *S. albulus* and any other ε-poly-L-lysine producer.

Item 25. The method for producing useful substances according to item 24, comprising transferring the expression vector according to any one of items 14 to 16 into the pls gene-defective or gene-disrupted strain.

Item 26. The method for producing useful substances according to any one of items 21 to 25, wherein the useful substances are compounds prepared by biosynthesis through a one-step or multi-step reaction.

Advantageous Effects of Invention

A recombinant ε-poly-L-lysine synthetase (recombinant Pls) that has never been previously produced in any conventional expression system can be efficiently produced and accumulated using the promoter, the expression vector, the host cell or the method for producing useful substances according to the invention. According to the invention, enhanced production of ε-poly-L-lysine is also achieved.

Moreover, desired useful substances can also be effectively produced by using the promoter, the expression vector, the host cell or the method for producing useful substances according to the invention.

BRIEF DESCRIPTION OF DRAWINGS

FIG. 1*a* is a graph showing pH of the culture broth (solid circle), an amount of ε-poly-L-lysine accumulated in the broth (open square) and an growth of bacterial cell (open triangle) upon aerobically cultivating *S. albulus* NBRC14147 in the ε-poly-L-lysine production medium for 30 hours in a Jar-fermentor. FIG. 1*b* is a diagram showing a photograph of agarose gel electrophoresis performed to assess total RNA extracted from the cells at each time point shown in FIG. 1*a*. FIG. 1*c* is a diagram showing a result of RT-PCR performed with total RNA.

FIG. 5a is a graph showing a time course of indigoidine production and pH of the culture broth (solid square and x-mark, respectively) upon aerobically cultivating a S. albulus Δpls/pDC009-bpsA strain in the $\epsilon$-poly-L-lysine production medium containing 25 μg/ml of apramycin and 50 μg/ml of neomycin at 30° C. in a 3 L Jar-fermentor, and a graph showing a time course of hyaluronic acid (HA) production and pH of the culture broth (solid rhombus and solid circle, respectively) upon aerobically cultivating a S. albulus Δpls/pDC009-mhasA strain in an $\epsilon$-poly-L-lysine production medium containing 25 μg/ml of apramycin and 50 μg/ml of neomycin at 30° C. in a 3 L Jar-fermentor. FIG. 5b is a graph showing time course of $\epsilon$-poly-L-lysine ($\epsilon$-PL) production and pH of the culture broth upon cultivating a S. albulus Δpls/pDC009-pls strain in a manner similar to cultivation in FIG. 5a. FIG. 5c is a graph showing ATP consumption during production of indigoidine and $\epsilon$-PL (calculated from the amounts of indigoidine and $\epsilon$-PL produced).

DESCRIPTION OF EMBODIMENTS

1. Promoter of the Invention

Figures 1, 2:
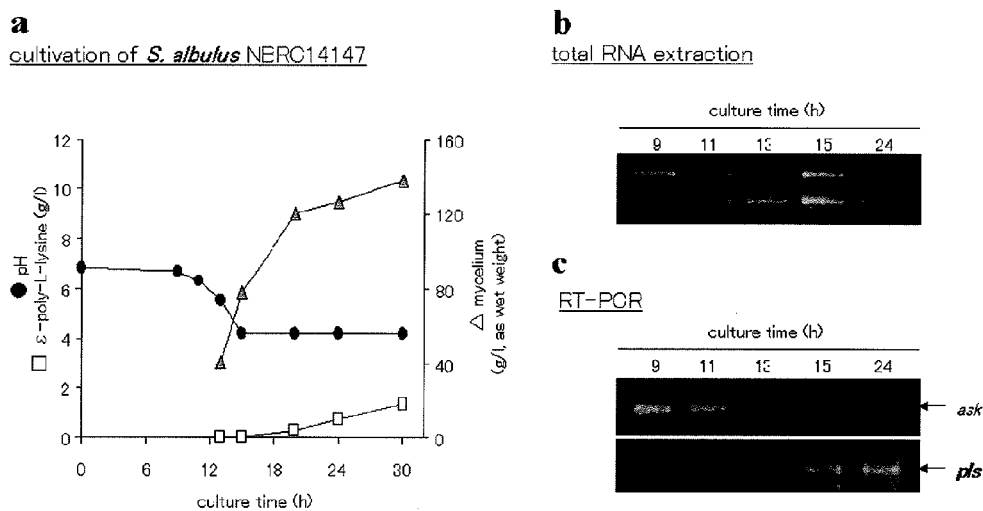
FIG. 2 is a diagram showing a predicted promoter region of the ε-poly-L-lysine biosynthetic gene cluster. Each number shows a distance from an initiation codon (ATG) of the pls gene, and an underline shows a predicted translation start site.

According to one embodiment, the invention provides a promoter for specifically inducing gene expression in and after a late logarithmic growth phase suitable for producing a secondary metabolite in an actinomycete, Streptomyces species.

A promoter sequence of the invention is typically derived from a genome of the actinomycete, Streptomyces species, and exists within an approximately 350 bp upstream region of an initiation codon (ATG) of the pls gene. The promoter of the invention typically includes a promoter including the nucleotide sequence of SEQ ID NO: 1, SEQ ID NO: 2, SEQ ID NO: 3 or SEQ ID NO: 4, but is not limited thereto. The promoter also includes a functional equivalent, namely, an arbitrary promoter that is derived from an $\epsilon$-poly-L-lysine producer strain, and specifically induces expression of an $\epsilon$-poly-L-lysine synthetase (pls) gene in and after the late logarithmic growth phase. The promoter sequence of the invention can be identified by searching a peripheral region of the pls gene cluster, for example, by using a promoter prediction program as specifically shown in Examples described later, or utilizing a method pursuant therewith. A promoter region of the invention can be identified, when necessary, by analyzing expression of the pls gene using the method specifically shown in Examples described later, or a method equivalent thereto.

Utilization of the promoter of the invention has an advantage that useful substances can be produced by catalysis of an arbitrary transgene product (enzyme protein or the like) because a high secondary metabolite production ability of the actinomycete, typically, the $\epsilon$-poly-L-lysine producer, particularly, S. albulus, and a strong and sustained ATP regeneration capability thereof (precursor supply capability) can be utilized in and after the late logarithmic growth phase. In order to produce desired useful substances, the promoter of the invention and an arbitrary objective gene cloned downstream (under regulation) thereof are carried in an expression vector, and can be transferred into the $\epsilon$-poly-L-lysine producer (S. albulus, for example). Alternatively, the arbitrary objective gene can be inserted into a chromosome of the $\epsilon$-poly-L-lysine producer (actinomycete, Streptomyces species (S. albulus), for example) under control of the promoter by homologous recombination or the like without using the expression vector. As the $\epsilon$-poly-L-lysine producer, a strain having the high secondary metabolite production ability and the strong and sustained ATP regeneration capability (precursor supply capability) in and after the late logarithmic growth phase, such as the S. albulus, is advantageously used.

"Promoter" herein means a region in which a RNA polymerase is bound at initiating m-RNA synthesis (transcription). Moreover, "pls promoter" means an approximately 343-bp upstream region of the pls gene.

Furthermore, "pls gene" herein means a gene that encodes an $\epsilon$-poly-L-lysine synthetase (see Yamanaka et al., Nat Chem Biol. 2008 December; 4(12): 766-72. Epub 2008 Nov. 9, and Patent document 1: JP 2008-263868 A).

The term "useful substances" or "useful compounds" herein means industrially useful substances, such as $\epsilon$-poly-L-lysine or the enzyme protein that synthesizes the $\epsilon$-poly-L-lysine, and substances that can be produced (directly or indirectly) in accordance with a method for producing useful substances according to the invention.

"High producer strain" herein for desired useful substances or useful compounds means a strain that produces the desired useful substances or useful compounds with a high efficiency and in mass.

The term "secondary metabolite" herein is used in referring to the secondary metabolite usually used in the relevant field. More specifically, primary metabolism refers to a biochemical reaction (energy metabolism, or biosynthesis of amino acid, protein, nucleic acid, for example) that is commonly observed in many organisms. On the contrary, some biosynthetic reactions have no important role on maintaining its own life cycle and accumulate a mass of alkaloid, terpenoid, phenols, an antibiotic, pigment or the like in various kinds of animals and plants or microorganisms. Such biosynthetic reactions are referred to as secondary metabolism, and substances such as the alkaloid produced thereby are referred to as the secondary metabolite. Many of the secondary metabolites are produced only during a specific period or only in a specific tissue of ontogenesis (see Iwanami Seibutsugaku Jiten (Biology Encyclopedia), 4th edition, first copy, issued on Mar. 21, 1996).

"Objective gene" or "target gene" herein means a gene encoding a desired arbitrary protein (or polypeptide), an enzyme protein that synthesizes the desired useful substances, or the like. Specific examples of the "objective gene" include a pls gene, a bpsA gene, a hasA gene, a mhasA gene, a hasB gene, a hasB homolog gene (sav5025), a hasD gene or a hasD homolog gene (sav3561) as shown in Examples described later, but are not limited thereto. The "objective gene" includes an arbitrary gene derived from both related and unrelated organism of $\epsilon$-poly-L-lysine producer, and a cluster of plurality of genes therefrom.

2. Expression Vector of the Invention

According to a further embodiment, the invention provides the expression vector carrying the promoter of the invention. The expression vector of the invention can be used for expression of a desired objective gene in the actinomycete, preferably, an actinomycete, Streptomyces species, further preferably, an $\epsilon$-poly-L-lysine-producing actinomycete. The ε-poly-L-lysine producer includes an arbitrary bacterial strain that is known to produce the ε-poly-L-lysine. Specific examples include an actinomycete, *Streptomyces* species (*S. albulus, S. mashuense, S. roseoverticillatus, S. lavendulae*), an actinomycete, *Kitasatospora* species (*K. kifnense*) and a filamentous fungus (*Epichloe* sp.), but are not limited thereto.

The expression vector of the invention may further include a terminator sequence at downstream of the promoter. The terminator sequence typically includes partially or wholly the nucleotide sequence of SEQ ID NO: 7 or SEQ ID NO: 8, but is not limited thereto. The terminator sequence also includes a functional equivalent thereof, more specifically, an arbitrary nucleotide sequence that functions as a terminator (signal of termination of transcription) in expression of the objective gene cloned under regulation of the promoter. The terminator sequence used in the expression vector of the invention can be found in a region downstream of the ε-poly-L-lysine biosynthetic gene cluster in *S. albulus*, for example. Stabilization and/or promotion of efficiency of transcription-translation of the objective gene can be achieved by including the terminator sequence in the expression vector of the invention.

The protein to be produced by using the expression vector of the invention may be produced as a fusion protein with a tag protein so as to be convenient for affinity purification. Therefore, the expression vector of the invention may include a tag coding sequence in addition to the objective gene. Specific examples of the tag coding sequence include the nucleotide sequence of SEQ ID NO: 9 or SEQ ID NO: 10 as shown in Examples described later. Specific examples of a tag to be fused include His-tag or glutathione S-transferase (GST)-tag, but are not limited thereto. Expression as a tag fusion protein provides an advantage that the affinity purification can be utilized in production (recovery) of a recombinant protein, for example.

Specific non-limiting examples of the expression vector of the invention are shown as an expression vector of SEQ ID NO: 13, SEQ ID NO: 14 or SEQ ID NO: 15 in the Examples of the invention.

3. Host Cell into which the Promoter or the Expression Vector of the Invention is Transferred According to a still further example, the invention provides a host cell harboring the objective gene cloned under control of the promoter of the invention, or the expression vector of the invention that includes the objective gene under control of the promoter is transferred. A cell that can be used as the host of the invention includes a cell of the actinomycete including *Streptomyces* species, *Kitasatospora* species and *Rhodococcus* species, but is not limited thereto. Typically, a cell of the ε-poly-L-lysine producer can be used as the host of the invention.

It is advantageous that the host cell of the invention is used for producing the arbitrary useful substances, because a more efficient production of the useful substances can be achieved. For example, as shown in Reference Examples and Examples described later, when a strain such as a *S. albulus* Δpls strain in which the pls gene is disrupted in advance is used, no consumption of secondary metabolite production ability and ATP regeneration ability in and after the late logarithmic growth phase is required for production of the ε-poly-L-lysine, a major metabolite of the strain.

4. Method for Producing Useful Substances

According to a still further embodiment, the invention also provides the method for efficiently producing the useful substances utilizing the promoter or the expression vector of the invention. The method includes expression of the objective gene under control of the promoter of the invention in the actinomycete, typically, the ε-poly-L-lysine producer.

Alternatively, an objective protein that is encoded by the objective gene may be produced by transferring the expression vector of the invention into the ε-poly-L-lysine producer using a technology well known to those skilled in the art.

Alternatively, the arbitrary useful substances may be produced by cultivating the host cell harboring the expression vector of the invention. Cultivation conditions (a cultivation liquid composition, a cultivation period or the like) may be varied by those skilled in the art for any purpose.

In the following, the invention will be explained in greater detail by way of Examples, but the scope of the invention is not limited to the Examples.

EXAMPLES

Reference Example

During the ε-poly-L-lysine fermentation, *S. albulus* shows characteristic ε-poly-L-lysine production profile; high levels of ε-poly-L-lysine production is observed only under acidic pH conditions of late-logarithmic growth phase that inhibits its own growth. This observation indicates that *S. albulus* preferentially utilizes L-lysine and ATP, as a precursor molecule and a energy source respectively, for the ε-poly-L-lysine production than for its growth (primary metabolism) under the acidic condition.

According to the report by Kahar et al. (J Biosci Bioeng. 2001; 91(2): 190-4), a *S. albulus* S410 strain (strain induced from *S. albulus* NBRC14147) produces and accumulates as high as 48.3 g/l of ε-poly-L-lysine in a culture broth in 8 days cultivation. Accordingly, the *S. albulus* or its derivatives can be referred to as a ε-poly-L-lysine high producer and simultaneously as a L-lysine high producer. Furthermore, ATP as another precursor is converted into AMP in association with an ε-poly-L-lysine synthetic reaction (JP 2008-263868 A). Therefore, although neogenesis of a certain ATP may occur in a cell of an ε-poly-L-lysine producer, a regeneration system from AMP to ATP obviously functions continuously and intensively.

The mass number per one lysine residue in the ε-poly-L-lysine is 128. Accordingly, the L-lysine residue in 48.3 g/l of ε-poly-L-lysine is approximately equal to an amount of 0.38 mol/l. Because an average polymerization degree of the ε-poly-L-lysine is 30 mer, the number of peptide bonds in one molecule is calculated to be 29 from an equation: 30−1=29. Because Pls requires one ATP molecule per single peptide bond formation (condensation reaction), an amount of ATP consumption is calculated to be 0.37 mol/l from an equation: 0.38 mol/l×29/30=0.37 mol/l. Therefore, 0.37 mol/l of ATP is consumed to produce 48.3 g/l of ε-poly-L-lysine during the cultivation for 8 days in the *S. albulus* S410 strain. The amount of ATP consumption is much larger than an amount of ATP regenerated by a thermostable polyphosphate kinase as described above (corresponding to as high as 203.9 g/l as ATP·2Na salt).

Accordingly, a gene expression system using the ε-poly-L-lysine producer, *S. albulus* NBRC 14147 or its derivatives as a host was considered to allow high levels of desired secondary metabolite production due to strong and sustained ATP regeneration capability of *S. albulus* under acidic conditions. Furthermore, the gene expression system was considered to be a powerful means for simultaneously solving the both objectives of the efficient ATP regeneration applicable to mass production of the useful substances, and the production of arbitrary useful substances by the actinomycete.

Moreover, disruption of a pls gene in *S. albulus* as a host in advance (*S. albulus* Δpls strain) was considered to allow more efficient production of desired useful substances because ability to produce secondary metabolite and regenerate ATP under acidic conditions wouldn't be used for the production of ε-poly-L-lysine, main product in this strain.

pLAE001, a *Escherichia coli-actinomycete* shuttle vector, which can be utilized in an actinomycete, *Streptomyces* species including *S. albulus*, has been already developed from a *S. albulus* cryptic plasmid pNO33 (JP 2005-237335 A). Moreover, pLAE003, as a derivative thereof and having an universally used resistant marker, aphII (kanamycin-neomycin resistance gene) (Hamano et al., J Biosci Bioeng. 2005 June; 99(6): 636-41), and pLAE006 in which a strong constitutive promoter (erm E) is added to pLAE003 have been constructed (Hamano et al., Appl Microbiol Biotechnol. 2007 September; 76(4): 873-82. Epub 2007 Jul. 5), and effectiveness thereof has also been assessed.

Accordingly, use of the *S. albulus* Δpls strain (JP 2008-263868 A) as the host, and pLAE006 as the gene expression vector was considered to allow achievement of an objective of industrial production of desired useful substances. In order to verify possibility thereof, the present inventors have verified as to whether or not utilization of the pLAE006 as the gene expression vector allows actual expression of the objective gene to give an active protein or enzyme and production of the secondary metabolite under acidic conditions in which ATP supply profile of the host, the *S. albulus* Δpls strain, can be utilized most effectively. Verification was conducted by introducing pLAE006 harboring the pls gene into the *S. albulus* Δpls strain, and confirming expression of an inserted gene product (ε-poly-L-lysine synthetase, Pls) from presence or absence of the ε-poly-L-lysine produced in a medium under acidic conditions. In the following, the method will be explained.

Then, pLAE006 pls constructed by inserting the pls gene (including a ribosome binding site upstream of the ORF and H is x8-tag coding sequence immediately before the termination codon) into a BamHI-HindIII site of pLAE006 was introduced into *S. albulus* Δpls by intergeneric conjugation with *Escherichia coli* S17-1 strain in accordance with the method described in Patent document 1. *S. albulus* Δpls/pLAE006-pls as the resultant transformant was aerobically cultivated in an ε-poly-L-lysine production medium containing 25 μg/ml of apramycin and 50 μg/ml of neomycin (Kahar et al., J Biosci Bioeng. 2001; 91(2): 190-4) at 30° C. for 48 hours.

After completion of the cultivation, when the amount of ε-poly-L-lysine produced in the culture supernatant was measured in accordance with a HPLC method as described in JP 2008-263868 A, production of the ε-poly-L-lysine was detected, but the amount was very small in only a trace extent. Moreover, purification of recombinant Pls was attempted by Ni affinity chromatography in accordance with an ordinary method. However, purified Pls could not be obtained because the amount of expression was very small.

A functional analysis of Pls was also partially performed using the present method (2009 Annual Meeting of The Society for Biotechnology, Japan, P. 194). The results described above show the objective of high production of useful substances by microorganisms is quite difficult even by induction of the gene expression from constitutive ermE promoter on pLAE006 because even the gene from itself en be hardly expressed under the acidic condition after the logarithmic growth phase.

Accordingly, a search for "promoter that specifically induces gene expression under acidic conditions in and after the logarithmic growth phase" suitable for producing substances in *S. albulus* was required.

Example 1

Analysis of a pls Gene Expression Profile by RT-PCR

In view of the fact that *S. albulus* produces a remarkable amount of ε-poly-L-lysine only under acidic conditions in and after a logarithmic growth phase, a possibility that the expression of the pls gene could be specifically induced only under the characteristic conditions was considered.

To clarify the possibility, expression profile of the pls gene was analyzed by RT-PCR method. In accordance with the method described in JP 2008-263868 A, *S. albulus* NBRC14147 was aerobically cultivated for 30 hours in a 3 L Jar-fermentor (FIG. 1a). Moreover, after a decrease in pH in association with cultivation, a 10% aqueous ammonia solution was appropriately fed to maintain culture pH at 4.2 suitable for ε-poly-L-lysine production.

During the cultivation, an aliquote was appropriately sampled to extract total RNA from a bacterial cell in accordance with an ordinary method (FIG. 1b). From the total RNA, the pls gene was subjected to reverse transcription (RT) using an ε-PL-NRPS-R primer as shown below and ReverTra Ace made by TOYOBO CO., LTD as a reverse transcriptase. Moreover, an aspartokinase gene (ask), a key enzyme for L-lysine synthesis, was also prepared in the same way by reverse transcription using an Ask-C4 primer shown below as a control.

```
ε-PL-NRPS-F;
                                    (SEQ ID NO: 16)
5'-GGGGGATCCTCGTCGCCCCTTCTCGAATCG-3'

ε-PL-NRPS-R;
                                    (SEQ ID NO: 17)
5'-ACCAAGCTTTCACGCGGCCGCACCTCCCTC-3'

Ask-C4;
                                    (SEQ ID NO: 18)
5'-ACCAAGCTTTCATCGCCCGGTGCCGCCGTA-3'

Ask-N4;
                                    (SEQ ID NO: 19)
5'-GGGGGATCCGGCCTTGTCGTGCAGAAGTAC-3'.
```

Then, PCR was performed with ε-PL-NRPS-F and ε-PL-NRPS-R primers using the resultant reverse transcript (pls gene) as a template. PCR was also performed with Ask-C4 and Ask-N4 primers also for the reverse transcript (ask gene) as the control in a similar manner (FIG. 1c).

As a result, the ask gene used as the control was demonstrated to be expressed from an initial phase of cultivation, and its expression level was remarkably decreased after a late logarithmic growth phase at which pH of culture broth starts dropping. Because Ask is the key enzyme for L-lysine synthesis, an ask gene expression profile closely associated with cell proliferation can be recognized to be reasonable.

Meanwhile, in contrast with the ask gene, the expression of the pls gene was detected in and after the late logarithmic growth phase at which a pH of the culture broth starts dropping, and the expression reached a maximum near pH 4.2 at which production of the ε-poly-L-lysine was detected. Moreover, expression with a high level was maintained even after 24 hours in which the cell growth was negligible. From the results of RT-PCR analysis described above, it was demonstrated that the expression of the pls gene was specifically induced from late logarithmic growth phase in which the cell growth is blunted to a stationary phase, and under a low pH environment suitable for producing a secondary metabolite.

Normally, gene expression (neogenesis of protein) hardly occurs near the stationary phase in which such cell growth is not detected. However, because the pls gene is specifically and sustainably expressed during the phase, regulation of the pls gene expression is likely to be unusual.

Moreover, as described above, several kinds of actinomycetes and certain filamentous fungi are known to produce the ε-poly-L-lysine. Both of the actinomycete and the filamentous fungus commonly produce the ε-poly-L-lysine only after pH of the cultures dropped to lower than pH 4.5. Accordingly, Pls enzymes in these producers are supposed to be specifically expressed in association with a decrease of culture pH.

From the result, using a gene expression vector having a promoter that regulates the pls gene expression to give a characteristic expression behavior, and an ε-poly-L-lysine producer strain as a host, it was considered to be applicable to the objective of producing arbitrary useful substances.

Example 2

Identification of a Promoter Region of a pls Gene (pls Promoter) and Construction of pDC007, a Recombinant Vector Having the Pls Promoter Identification of a promoter region related to regulation of pls gene expression was attempted. A DNA sequence of 33-kb including a pls gene has been already disclosed (GeneBank, accession No. AB385841). Moreover, a metalloprotease gene translationally-coupled with downstream of the pls gene has also been demonstrated to be a major ε-poly-L-lysine degrading enzyme (PldII, end type) gene in *S. albulus* (Proceedings of 2008 Annual Meeting of The Society for Biotechnology, Japan, p. 206). Therefore, the pls gene and a pldII gene can be recognized to form an ε-poly-L-lysine biosynthetic gene cluster. When flanking region of the gene cluster was analyzed by a Neural Network Promoter Prediction (www.fruitfly.org/seq_tools/promoter.html) program, no promoter region that gives a significant score (larger than 0.8) was found.

Then, when a search was conducted again with lowered threshold (larger than 0.4), three predicted promoter regions shown in FIG. 2 were found. However, all three regions has a low score, and thus the promoter region was not identified. Moreover, in detailed analysis of flanking resion of the gene cluster, a terminator sequence was found directly downstream of the gene cluster, but no regulatory gene was found.

However, no other promoter candidate regions existed in the peripheral region. Thus, the promoter region of the cluster was supposed to be any one of the three predicted regions described above. Therefore, inclusion of the promoter of the cluster in any one of the three predicted regions was verified in accordance with the method described below.

All of the three predicted regions were located within 350-bp upstream of a pls gene initiation codon (ATG). Therefore, 343-bp region including all three predicted promoters was amplified from *S. albulus* chromosomal DNA by PCR with eplP-F and eplP-R primers as shown below. The PCR amplified fragment was inserted into a FseI-BamHI site of the pLAE003 to construct pDC007 shown in FIG. 3.
Formula 1
eplP-F; 5'-ACTAT<u>GGCCGGCC</u>GTTGGTCGACGTCC-3' (SEQ ID NO: 20) (an underlined part represents a FseI site)
eplP-R; 5'-AGGAA<u>GGATCC</u>CATATGTATGCCTCTGTTCGGTGC-3' (SEQ ID NO: 21) (an underlined part represents a BamHI site, and a sequence within an enclosure ☐ represents a newly introduced NdeI site).

Next, a function and effectiveness of the vector were verified by a expression experiment using the pls gene described below. After the pls gene was subjected to PCR amplification according to PCR with plsnde-F and plshind-R primers using the *S. albulus* chromosomal DNA as the template, an amplified fragment was digested with restriction enzymes NdeI and HindIII.

```
plsnde-F;
                                          (SEQ ID NO: 22)
5'-GGAATTCCATATGTCGTCGCCCCTTCTCG-3'
(an underlined part represents an NdeI site)

plshind-R;
                                          (SEQ ID NO: 23)
5'-ACCCAAGCTTTCACGCGGCCGCACCTCC-3'
(an underlined part represents a HindIII site).
```

The pls gene digested with the restriction enzymes was inserted into an NdeI-HindIII site located downstream of a predicted pls promoter on pDC007 to construct pDC007 pls, and the pDC007-pls was transferred into *S. albulus* Δpls by conjugal transfer from *Escherichia coli* S17-1 strain in accordance with the method described in Non-patent document 4. The resultant transformant, *S. albulus* Δpls/pDC007-pls, was aerobically cultivated in an ε-poly-L-lysine production medium containing 25 μg/ml of apramycin and 50 μg/ml of neomycin at 30° C. for 30 hours in a 3 L Jar-fermentor in accordance with the method described in JP 2008-263868 A.

After completion of the cultivation, an amount of ε-poly-L-lysine in culture supernatant was quantitatively determined. As a result, the *S. albulus* Δpls/pDC007 strain into which only the recombinant vector was transferred (no insertion of the pls gene) obviously lacked ε-poly-L-lysine production ability due to disruption of the pls gene. However, production and accumulation of a remarkable amount of ε-poly-L-lysine were detected in the culture of the *S. albulus* Δpls/pDC007-pls strain into which pDC007-pls was transferred.

The amount of production was 1.32 g/l in cultivation for 30 hours in Although the parental strain of *S. albulus* Δpls (as disclosed in JP 2005-237335 A, a native plasmid pNO33-cured *S. albulus* strain that shows equal ε-poly-L-lysine productivity to that of *S. albulus* NBRC14147) showed ε-poly-L-lysine productivity at 1.32 g/l in 30 h cultivation. *S. albulus* Δpls/pDC007-pls strain surprisingly showed the productivity of 2.73 g/l, which was twice higher than that of wild strain (NBRC14147).

From the result described above, the region for regulating expression of ξ-poly-L-lysine biosynthetic gene cluster (pls promoter) was identified to be in a 343-bp upstream range of the pls gene initiation codon (ATG). Accordingly, in the following, the 343-bp upstream region of the pls gene initiation codon (ATG) is referred to as the pls promoter (SEQ ID NO: 4) herein.

Moreover, the promoter region was identified and simultaneously utilized, resulted in successfully achieving the subject of constructing the gene expression vector pDC007 that specifically induces expression of the objective gene under acidic conditions in and after a logarithmic growth phase in which supply of a secondary metabolite synthetic precursor is enhanced in *S. albulus*.

The result demonstrates that recombinant Pls expressed under control of the pls promoter has synthesized the ε-poly-L-lysine as an objective compound by utilizing ATP subjected to regeneration (partially including neogenesis also) in a cell of the *S. albulus* Δpls strain, and effectiveness of *S. albulus* and the gene expression vector having the pls promoter was verified as a tool for producing useful substances.

Moreover, a ε-poly-L-lysine high producer also successfully established beyond expectation was by utilizing the vector. The reason for improving the productivity is supposed to be that the pls gene originally existing only one copy on a chromosome was introduced with the vector, and thus multi-copies of the pls gene existed in a host cell, as a result, an amount of Pls accumulated as a translation product and also an amount of ε-poly-L-lysine produced as a Pls reaction product were improved.

Accordingly, the result of the Example shows effectiveness of the pls promoter and *S. albulus* as a host for producing arbitrary useful substances. A vector region other than the pls promoter of the recombinant vector is considered to be not necessarily a derivative of pLAE001 or 003 having an autonomously replicating region of pNO33 used in the Example, if the vector region can be autonomously replicated stably in the host ε-poly-L-lysine producer. Moreover, from the same reason, it is expected that more remarkable effect of the pls promoter can be obtained with higher copy number of the vector. Furthermore, a similar effect is considered to be obtainable even without using the expression vector if an arbitrary objective gene is inserted into the chromosome of *S. albulus* under control of the pls promoter by homologous recombination, although an amount of objective product production may be decreased to some extent because an effect of the copy number can not be obtained.

Moreover, as described above, several kinds of actinomycetes and certain filamentous fungi are known to produce the ε-poly-L-lysine. Also in these producer strains, expression of Pls is considered to be specifically induced in association with a decrease in pH of the culture broth. Accordingly, a similar effect is considered to be obtained even using a promoter region of ε-poly-L-lysine biosynthetic gene cluster derived from an ε-poly-L-lysine producer other than *S. albulus*.

According to genomics in recent years, a number of genes and gene clusters (clusters) that are considered to perform biosynthesis of a new secondary metabolite from various kinds of actinomycetes are found. These genes (and clusters) are under control of a potentially weak or nonfunctional promoter. Therefore, most of the genes (and clusters) actually do not produce a secondary metabolite, and have escaped through exploratory researches energetically conducted for useful physiologically active substances all over the world. Accordingly, a new way for a search of new physiologically active substances and a research for production thereof is possibly opened by utilizing a newly found pls promoter of the invention in place of a potential promoter of the secondary metabolite biosynthesis genes (and clusters) to forcibly express the genes (and clusters), and to actually produce the secondary metabolite by utilizing an abundant precursor in *S. albulus*. In this regard, too, the gene induction expression system of the invention is effective.

Example 3

Construction of a pDC007 Derivative

Subsequently, a pDC007 derivative was constructed in order to apply a gene expression vector having a pls promoter according to the invention not only as a tool for producing useful substances but also for producing a recombinant protein.

In order to suppress read through by a RNA polymerase and to stabilize transcription-translation and promote efficiency thereof, a terminator sequence found downstream of an ε-poly-L-lysine biosynthetic gene cluster was introduced into downstream of a multiple-cloning site of pDC007 in accordance with the method described below.

Figure 3:
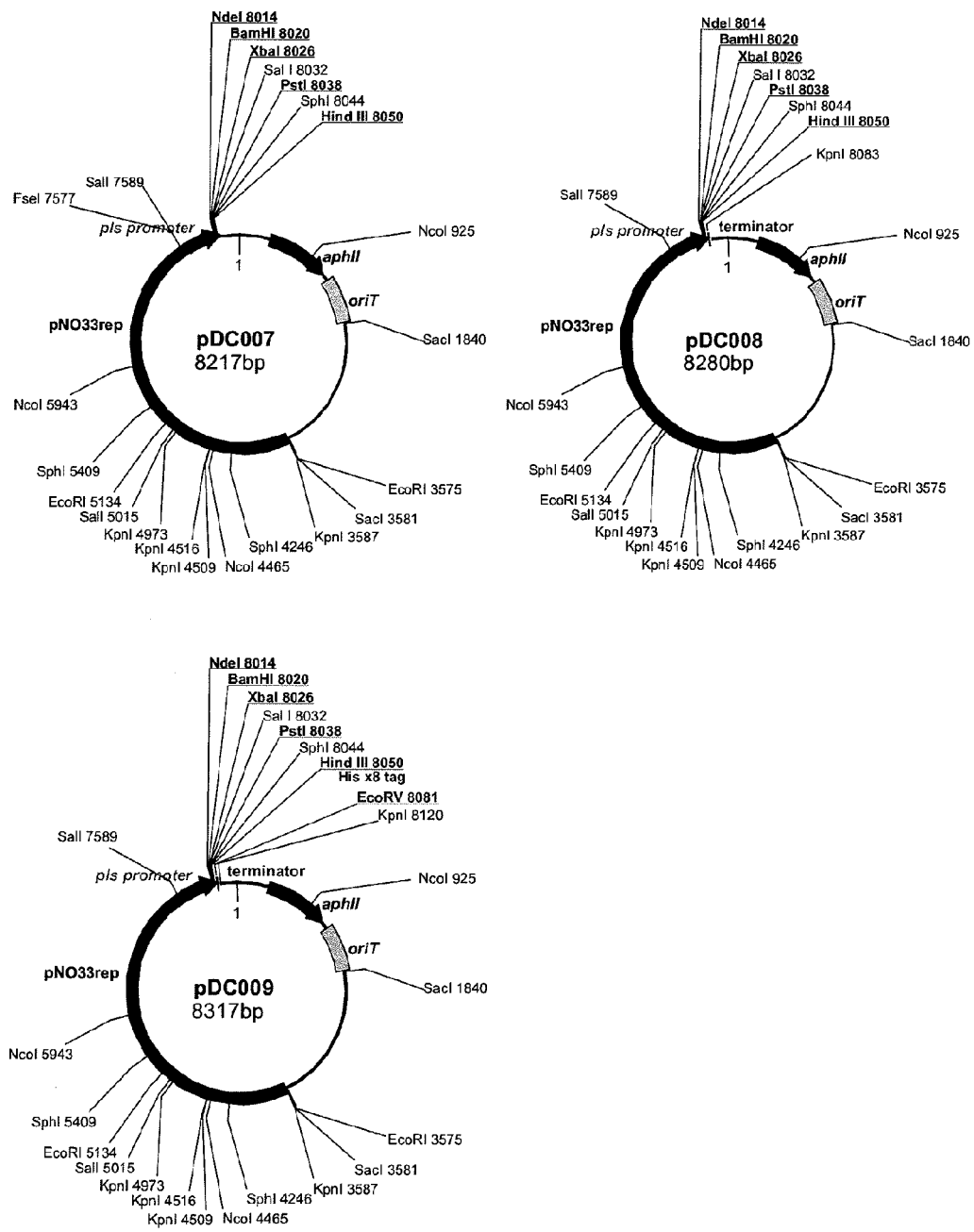
FIG. 3 is a map of vectors that have inducible pls promoter for gene expression available in an actinomycete, Streptomyces species.

Based on the terminator sequence (an underlined part in the sequence described below) found immediately downstream of the cluster, two mutually complementary single-stranded oligo DNA, Term-F and Term-R shown below, were synthesized. After mixing the DNAs, heating and cooling were carried out to form a double-stranded DNA, which was then inserted into a PstI-HindIII site of pDC007 to construct pD008 as shown in FIG. 3.

```
Term-F;
                                       (SEQ ID NO: 5)
5'-GGCATGCAAGCTTGAGCGCTCCGCGTGCCCGGTGGCGGACGGTAC CCCGTCCGCCACCGGGCACGGCCGGC-3'
(an underlined part represents a predicted
terminator region)

Term-R;
                                       (SEQ ID NO: 6)
5'-AGCTGCCGGCCGTGCCCGGTGGCGGACGGGGTACCGTCCGCCACC GGGCACGCGGAGCGCTCAAGCTTGCATGCCTGCA-3'.
(an underlined part represents a predicted
terminator region)
```

In producing the recombinant protein, a vector is more advantageous when the vector can be expressed a protein as tag-fused protein allowing affinity purification. Therefore, based on pDC008 constructed in accordance with the method described above, a derivative that can express an inserted gene product as a C-terminal His-tag fused protein was constructed.

Two mutually complementary types of single-stranded oligo DNA as His8C-F and His8C-R shown below were prepared. After mixing the DNAs, heating and cooling were carried out to form a double-stranded DNA, which was then inserted into a PstI-HindIII site of pDC008 to construct pD009 as shown in FIG. 3.

Formula 2
His8C-F;
5'-GGCATGCAAGCTT
CACCACCACCACCACCACCACCACTGATATCC-3'
(SEQ ID NO: 9) (an underlined part represents a Hisx8-tag region and a sequence surrounded by an enclosure represents a termination codon)

His 8C-R;
5'-AGCTGGATATCA
GTGGTGGTGGTGGTGGTGGTGGTGAAGCTTGCATGC
CTGCA-3' (SEQ ID NO: 10) (an underlined part represents a Hisx8-tag region and a sequence surrounded by an enclosure □ represents a termination codon).

Example 4

Establishment of αε-poly-L-Lysine High Producer, and Expression and Purification of Recombinant Pls In order to assess that a gene expression vector having a pls promoter according to the invention is also effective to produce a recombinant protein, production and purification were attempted for recombinant Pls using pDC009 that can express the inserted gene product as a C-terminal His-tag fused protein.

After the pls gene was amplified from *S. albulus* chromosomal DNA by PCR with plsnde-F and plshindhis8-R primers described below, the fragment was digested with restriction enzymes NdeI and plsnde-F; 5'-GGAATTC CATATGTCGTCGCCCCTTCTCG-3' (SEQ ID NO: 24) (an underlined part represents an NdeI site)
plshindhis8-R; 5'-GTGGTG AAGCTTCGCGGCCGCACCTC-3' (SEQ ID NO: 25) (an underlined part represents a HindIII site).

The digested pls gene was inserted into an NdeI-HindIII site of pDC009 to construct pDC009 pls, which was then transferred into *S. albulus* Δpls by conjugal transfer with *Escherichia coli* S17-1 strain in accordance with the method described in Non-patent literature No. 4. *S. albulus* Δpls/pDC009-pls as the resultant transformant was aerobically cultivated in an ε-poly-L-lysine production medium containing 25 μg/ml of apramycin and 50 μg/ml of neomycin at 30° C. for 30 hours in a 3 L Jar-fermentor according to the method described in JP 2008-263868 A.

After completion of the cultivation, an amount of ε-poly-L-lysine in cultivation supernatant was quantitatively determined according to a HPLC method described in JP 2008-263868 A. As a result, a *S. albulus* Δpls/pDC009-pls strain showed a productivity of 3.21 g/l of ε-poly-L-lysine. The productivity was further improved, as compared with the productivity using the *S. albulus* Δpls/pDC007-pls strain described above. The reason therefor is considered to be that transcription-translation was stabilized or efficiency thereof was promoted by a terminator sequence arranged downstream of a multiple-cloning site.

Next, 15 g (wet weight) of bacterial cells recovered by centrifugation was resuspended in 45 ml of a homogenization buffer containing 50 mM Tris-HCl (pH 7.8), 30% (w/v) glycerol, 0.5 M NaCl, 2% (w/v) Triton X-100 and 5 mM DTT, subjected to sonication and subsequent centrifugation in accordance with the method described in JP 2008-263868 A, and the resultant supernatant was used as a crude enzyme. In accordance with an ordinary method, His-tag fused recombinant Pls was purified by using a chromatography carrier for His-tag fusion protein purification, Ni Sepharose 6 Fast Flow (made by GE Healthcare Corporation).

Figure 4:
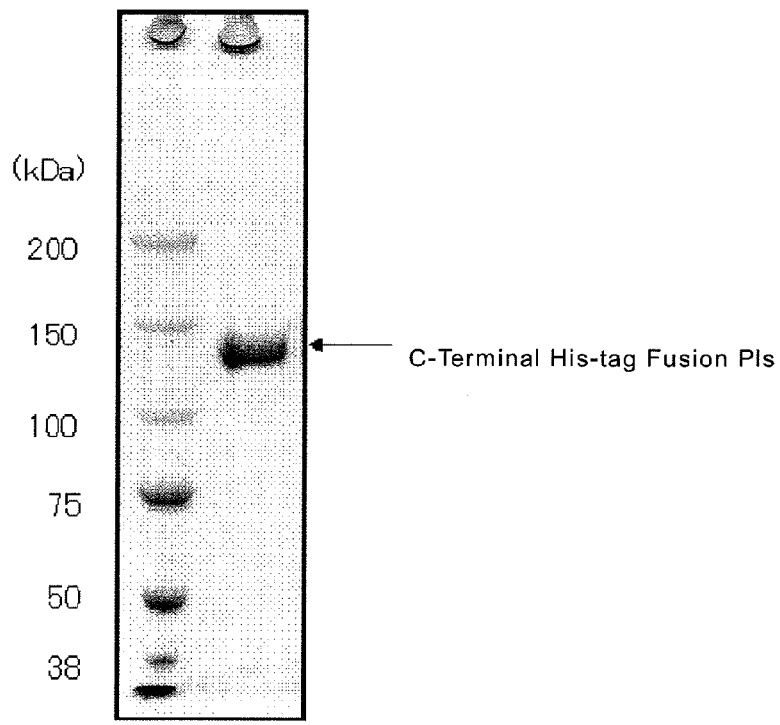
FIG. 4 is a diagram showing results of SDS-PAGE analysis of recombinant C-terminal His-tag fused Pls purified from a S. albulus Δpls/pDC009-pls strain.

As a result, as shown in SDS-PAGE analytical results in FIG. 4, purified recombinant Pls with a high purity was obtained, and a yield (amount of protein) of the purified recombinant Pls as measured in accordance with the method described in JP 2008-263868 A was 1.8 mg. Since Pls is a membrane-bound enzyme having six transmembrane domains, it takes long time to get purified Pls, and a yield is only approximately 2.9 mg of from 70 g of bacterial cell (JP 2008-263868 A). Accordingly, the yield has been improved 3 times higher.

It is well known that a construction of a recombinant transmembrane protein is not easy. Similarly, since Pls is a membrane protein with six transmembrane domains, a construction of the recombinant Pls was quite difficult even using any of general purpose gene expression systems in which microorganisms such as *Escherichia coli*, a yeast and also an actinomycete, *Streptomyces lividans* are used as a host. However, it was made possible by sustainably expressing the pls gene under control of the pls promoter for specifically inducing gene expression under a low pH environment in and after a late logarithmic growth phase that the high producer strain for ε-poly-L-lysine could be established, and also the recombinant Pls that had not been previously produced as functional enzyme was successfully produced and accumulated.

As described above, effectiveness of the pls promoter and the gene expression vector having the pls promoter according to the invention was shown by using the pls gene. It is obviously possible that, by inserting an industrially important gene into the vector in a similar manner for transformation of *S. albulus* Δpls, production of the arbitrary useful substances utilizing high precursor supply ability of the host for secondary metabolite biosynthesis at a maximum level can also be achieved. In this case, precursors for biosynthesis of an arbitrary substance can also be exogenously added to the system if the precursor other than ATP runs short.

The gene induction expression system using *S. albulus* and the gene expression vector having the pls promoter according to the invention is not a so-called high expression system such as a pET system in *Escherichia coli*. However, because many of secondary metabolites are generally produced under limited conditions in a late phase of cultivation, it is not necessarily preferable that the gene is expressed constitutively (permanently) and in large quantities from an initial phase of cultivation for achieving an objective of producing the secondary metabolites by recombinant microorganisms. Moreover, even a system allowing induction regulation of gene expression does not fully function in many cases in the late phase of cultivation suitable for production of secondary metabolites in which protein neogenesis hardly occurs. In this regard, too, the gene induction expression system of the invention is effective.

Example 5

Production of Arbitrary Compounds Other than ε-Poly-L-Lysine (1)

Effectiveness was assessed for the promoter and the recombinant vector having the promoter, and also the method for producing arbitrary useful substances using *S. albulus* as a host according to the invention by the method described below. A bpsA gene in a D-cycloserine-producing actinomycete, *Streptomyces lavendulae*, encodes a single module type non-ribosomal peptide synthetase and functions as a biosynthesis gene for a blue pigment, indigoidine (Takahashi et al. (J Biol Chem. 2007 Mar. 23; 282(12): 9073-81. Epub 2007 Jan. 19; JP 2007-189969 A).

A product of the gene, BpsA, catalyzes a reaction for forming one indigoidine molecule from two L-glutamine molecules and two ATP molecules as a substrate. Accordingly, effectiveness of the gene induction expression system of the invention can be easily assessed by expressing the bpsA gene with a host-vector system of the invention, quantitatively determining an amount of blue pigment (indigoidine) to be produced, and further calculating an amount of ATP consumption in the reaction from the amount of pigment.

Then, the effectiveness of the gene induction expression system of the invention was assessed also for producing arbitrary substances using a gene derived from a heterogeneous actinomycete, bpsA gene from *S. lavendulae* NBRC 12340 (a strain identical with ATCC11924 described in Takahashi et al. (J Biol Chem. 2007 Mar. 23; 282(12): 9073-81. Epub 2007 Jan. 19, and JP 2007-189969 A).

After the bpsA gene was amplified from *S. lavendulae* chromosomal DNA by PCR with bpsAnde-F and bpsAhind-R primers described below using, the amplified fragment was digested with restriction enzymes NdeI and HindIII.

bpsAnde-F; 5'-GGAATTC
CATATGACTCTTCAGGAGACCAGCGTGCTCGAG-3'
(SEQ ID NO: 26) (an underlined part represents an NdeI site as a restriction enzyme)
bpsAhind-R; 5'-CCC
AAGCTTCTCGCCGAGCAGGTAGCGGATGTGC-3'
(SEQ ID NO: 27) (an underlined part represents a HindIII site as a restriction enzyme).

A fragment digested with the restriction enzyme was inserted into an NdeI-HindIII site of pDC009 to construct pDC009-bpsA, which was then transferred into *S. albulus* Δpls by intergeneric conjugation with *Escherichia coli* S17-1 strain. *S. albulus* Δpls/pDC009-bpsA as the resultant transformant was aerobically cultivated in an ε-poly-L-lysine production medium containing 25 µg/ml of apramycin and 50 µg/ml of neomycin at 30° C. in a 3 L Jar-fermentor in accordance with the method described in JP 2008-263868 A. Here, in consideration of water-insolubility of indigoidine to be produced, a cultivation period of time was limited up to 21 hours after starting the cultivation (approximately 10 hours after pH of the culture broth decreased to approximately 4.0, namely, induced gene expression). Although no color change of the culture broth was observed before its pH decreased from an initial value, a significant blue stain of the culture was observed after pH decreased.

After completion of the cultivation, the blue pigment produced in the culture broth was recovered together with bacterial cells by high-speed centrifugation. The resultant precipitate was resuspended in water and methanol, and then subjected to high-speed centrifugation again to wash the blue pigment and the bacterial cells. After the operation was further repeated twice to fully wash the blue pigment and the bacterial cells, precipitate was dried. Dimethylformamide (DMF) was added to the dry substance containing the blue pigment, followed by thorough sonication until the blue pigment was dissolved, and then bacterial cell residues were removed by high-speed centrifugation and a 0.2 micrometer membrane filter. The resultant solution was used as a crude blue pigment solution. Then, in accordance with the method described in JP 2007-189969 A, an excessive amount (ten times in volume) of pure water was added to the resultant crude blue pigment solution to precipitate the blue pigment, and the blue pigment was recovered by high-speed centrifugation and dried. The resultant dry substance was used as a purified blue pigment.

λmax of the purified blue pigment in DMF was 600 nm. Moreover, an EI-MS spectrum (m/z=248) also showed good agreement with the measured value of indigoidine as described in Takahashi et al. (J Biol Chem. 2007 Mar. 23; 282(12): 9073-81. Epub 2007 Jan. 19). Thus, the blue pigment produced with *S. albulus* Δpls/pDC009-bpsA was determined to be indigoidine.

Figure 5:
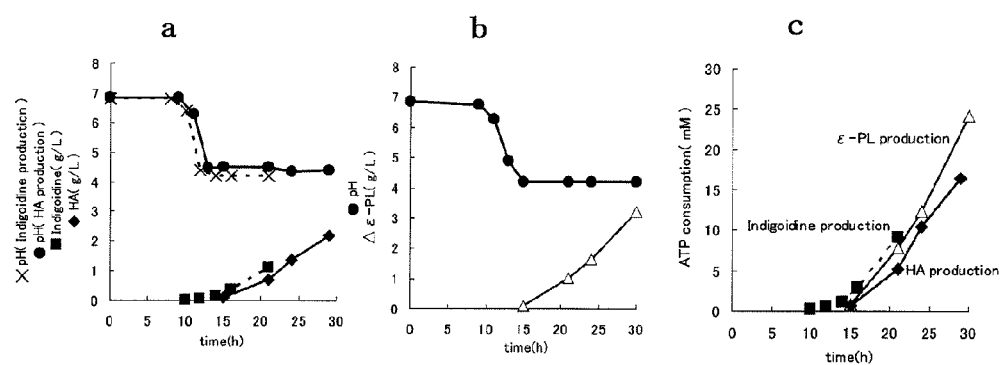

The productivity of indigoidine was measured according to spectrophotometry at a wavelength of 600 nm in DMF (logs=4.37). As a result, rapid production and significant accumulation of indigoidine were detected after pH of the culture broth dropped to approximately 4.2, and an amount of production thereof reached 1.13 g/l in cultivation for only 21 hours (FIG. 5a). Moreover, an amount of ATP per 1 L of medium to be consumed in indigoidine synthesis (calculated from the amount of indigoidine production) was equivalent to the amount of ATP consumption in producing ε-poly-L-lysine in the *S. albulus* Δpls/pDC009-pls strain (FIGS. 5b, c).

The result shows that even a gene from a heterogeneous organism can be expressed specifically and efficiently in a late logarithmic phase suitable for producing a secondary metabolite by using the host-vector system of the invention, and also that indigoidine as an objective compound was synthesized by utilizing virtually 100% of theoretically available ATP which is strongly regenerated in a *S. albulus* cell (partially including neogenesis also).

Surprisingly, the *S. albulus* Δpls strain produced a remarkable amount of indigoidine without using exogenous L-glutamine as a precursor. The finding shows that *S. albulus* per se also synthesized a remarkable amount of L-glutamine required for producing indigoidine. The mechanism to supply significant amount of L-glutamine is unclear. *S. albulus* may have a mechanism for keeping a constant intracellular pool of not only ATP but also a compound such as consumed amino acids in the cell.

Example 6

Production of Arbitrary Compounds Other than ε-Poly-L-Lysine (2)

In producing compounds such as ε-poly-L-lysine and indigoidine in which ATP is required directly and in a one-step reaction, effectiveness was assessed for the promoter, the recombinant vector having the promoter, and also the method for producing arbitrary useful compounds using *S. albulus* as the host according to the invention. However, many of natural useful compounds are biosynthesized through a multiple reaction, and ATP is required indirectly for the biosynthesis in many cases. Therefore, verification was conducted in accordance with the method described below as to whether or not the promoter, the recombinant vector having the promoter, and also the method for producing arbitrary useful compounds using *S. albulus* as the host according to the invention can be applied also for producing arbitrary compounds in which the compounds are biosynthesized through the multiple reaction in which ATP is required indirectly.

Figure 6:
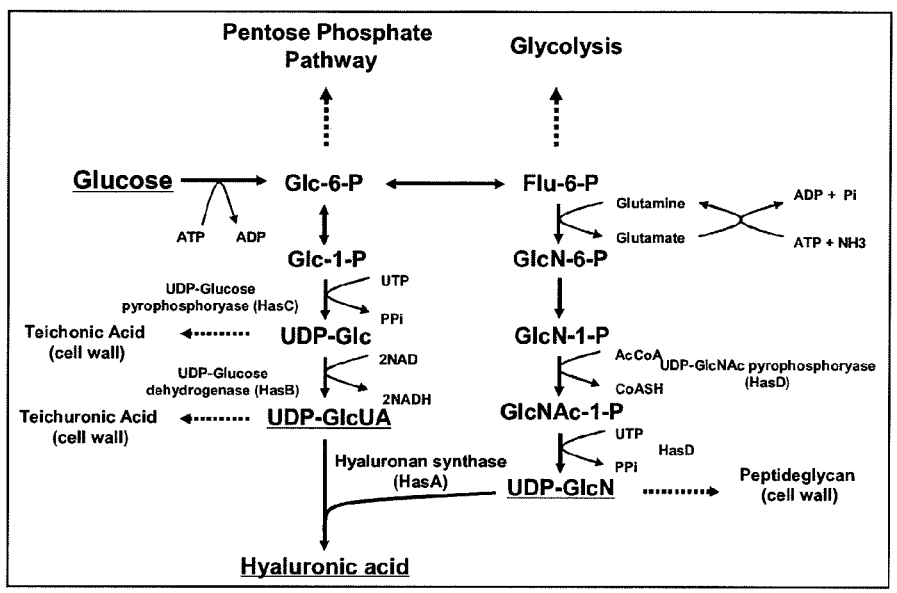
FIG. 6 is a diagram showing a biosynthetic pathway from glucose to hyaluronic acid.

A hasA gene in pathogenic lactic acid bacterium, *Streptococcus zooepidemicus*, encodes a hyaluronan synthetase, and a product of the gene, HasA, synthesizes hyaluronic acid comprising from a repetitive structure of glucuronic acid and N-acetyl glucosamine from UDP-N-acetyl glucosamine and UDP-glucuronic acid as a substrate (J Mol Evol. 2008 July; 67(1): 13-22. Epub 2008 Jun. 13). As shown in FIG. 6, three ATP molecules are required indirectly for synthesis of a disaccharide unit of glucuronic acid and N-acetyl glucosamine as a constituent saccharide of a final product, the hyaluronic acid, from glucose. Therefore, effectiveness of the invention was verified in regard to production of the hyaluronic acid.

HasA is a membrane-bound enzyme. Furthermore, codon usage in actinobacteria whose gene has an average GC content of approximately 70% is significantly different from that in lactic acid bacteria whose gene has an average GC content of approximately 40%. Thus, it was supposed that the native hasA gene from *Streptococcus zooepidemicus* was not functionally expressed in *S. albulus*. Therefore, in order to functionally express the hasA gene in *S. albulus*, the hasA gene in the lactic acid bacterium *Streptococcus zooepidemicus* was redesigned (40% GC to 63% GC) by optimization of codon usage definitive to the actinomycete, and thus artificial gene mhasA (SEQ ID NO: 28) was synthesized.

Moreover, in order to efficiently produce the hyaluronic acid in *S. albulus*, UDP-glucuronic acid and N-acetyl glucosamine as precursors for hyaluronic acid synthesis need to be supplied in a sufficient amount. Accordingly, an UDP-glucose dehydrogenase gene (hasB) as an enzyme having UDP-glucuronic acid synthesis activity and an UDP-N-acetyl glucosamine pyrophosphorylase gene (hasD) were coexpressed with the codon optimized hasA (mhasA) gene and the method described below.

The hasB gene homolog, sav5025, from *Streptomyces avermitilis* found by database search was amplified from *Streptomyces avermitilis* NBRC14893 chromosomal DNA by PCR with sav5025-assembleF and sav5025-hindR primers. sav5025-assembleF;

```
                                      (SEQ ID NO: 29)
5'-CTCGCATGAGCCTCAAGATCACCGTGATCGGCACCGG-3' sav5025-assembleR;
                                      (SEQ ID NO: 30)
5'-ATGGCGCTCATGCGGTGGCCTCCCCCATCGCGCGGTACGTCCA
GC-3'.
```

In a similar manner, a hasD gene homolog, sav3561 found in *Streptomyces avermitilis* genome by database search was amplified by PCR with sav3561-assembleF and sav3561-hindR primers.

sav3561-assembleF;

```
                                      (SEQ ID NO: 31)
5'-CGATGGGGGAGGCCACCGCATGAGCGCCATCCGCCCGGCAGCCGT-3' sav3561-hindR;
                                      (SEQ ID NO: 32)
5'-CCCAAGCTTTCAGTCTTCGCCTTCCGGCTTCCGGGAA-3'.
(an underlined part represents a restriction
enzyme HindIII site)
```

Figure 7:
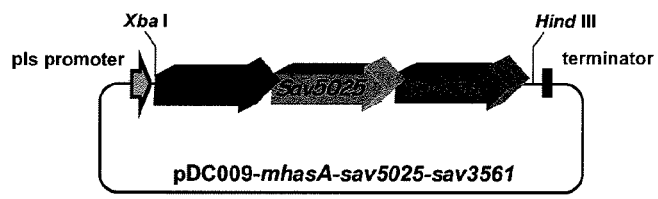
FIG. 7 is a diagram schematically showing an artificial hyaluronic acid biosynthetic gene cluster in which mhasA, sav5025 and sav3561 genes are translationally coupled.

Next, the mhasA gene, the sav5025, and sav3561 genes were assembled into a single fragment according to an overlap extension PCR method to construct an artificial hyaluronic acid biosynthetic gene cluster in which the mhasA, sav5025 and sav3561 genes were coupled (FIG. 7, SEQ ID NO: 33).

The gene cluster (mhasA-sav5025-sav3561) was subjected to restriction enzyme digestion with XbaI and HindIII, and then inserted into a XbaI-HindIII site of pDC009 to construct pDC009-mhasA-sav5025-sav3561. Because the gene cluster is designed to be transcribed as a single unit by the promoter of the invention, and a ribosome binding sites are provided upstream of each gene, each gene can be efficiently translated. Moreover, as a control, pDC009-mhasA in which only mhasA was inserted into XbaI-HindIII of pDC009 was simultaneously constructed. These constructs were introduced into *S. albulus* Δpls by intergeneric conjugation with *Escherichia coli* S17-1 strain, and *S. albulus* Δpls/pDC009-mhasA-sav5025-sav3561 and *S. albulus* Δpls/pDC009-mhasA as the resultant transformants were aerobically cultivated in an ε-poly-L-lysine production medium containing 25 µg/ml of apramycin and 50 µg/ml of neomycin at 30° C. in a 3 L Jar-fermentor in accordance with the method described in JP 2008-263868 A.

After completion of the cultivation, a cultivation liquid was provided for centrifugal separation to remove bacterial cells. To the resultant cultivation supernatant, Three volumes of ethanol was added to the supernatant to precipitate polysaccharides containing the hyaluronic acid, and the precipitates were recovered by centrifugation. Subsequently, after the precipitates were dissolved in a 0.3 mol/L sodium chloride aqueous solution, three volumes of ethanol was added again to precipitate polysaccharides. Then the precipitates were dissolved in deionized water and recovered as a crude sample.

The content of hyaluronic acid produced was measured in accordance with a carbazole-sulfuric acid method (Anal Biochem. 1962 October; 4: 330-4).

As a result, no production of hyaluronic acid was detected in the culture broth of *S. albulus* Δpls/pDC009-mhasA. However, *S. albulus* Δpls/pDC009-mhasA-hasB-sav3561 produced remarkable amount of hyaluronic acid after pH of the culture broth decreased to approximately 4.2, and the productivity thereof reached 2.2 g/l in cultivation for only 30 hours (FIG. 5a). Moreover, an amount of ATP per 1 L of medium to be consumed in hyaluronan synthesis (calculated from the amount of hyaluronic acid production) was substantially equivalent to the amount of ATP consumption in producing ε-poly-L-lysine in a *S. albulus* Δpls/pDC009-pls strain (FIGS. 5b, c). Moreover, the result shows that the hyaluronic acid as an objective compound was synthesized by efficiently utilizing theoretically available ATP which is strongly regenerated in a *S. albulus* cell (partially including neogenesis also).

From the result described above, the invention has been proved to be very effective in producing useful substances biosynthesized through the multiple reaction, and also in producing compounds in which ATP is required indirectly for the biosynthesis.

Any and all arbitrary useful compounds, without limiting to poly-lysine, indigoidin and hyaluronic acid, can be produced in large quantities using the promoter, the recombinant vector having the promoter, and *S. albulus* as the host according to the invention, and also applying a procedure in a manner similar to the Examples, such as codon modification of transgene and reinforcement of a precursor supply gene, when necessary.

Moreover, according to the Examples shown herein relating to productivity of substances, the productivity is evaluated within a relatively short period of time without resupplying carbonhydrates in fermentation process. However, when carbonhydrates consumed are sustainably fed, production and accumulation of the objective compound can be sustained for approximately eight days in the method for producing useful substances according to the invention in the same manner as the production of ε-poly-L-lysine as described in Kahar et al. (J Biosci Bioeng. 2001; 91(2): 190-4).

Example 7

Host Suitability for a pls Promoter

Function of a pls promoter was verified not only in *S. albulus* but also in any other actinomycete, particularly, an ε-poly-L-lysine non-producer in accordance with the method described below.

pDC009-pls that has been already constructed in Example 4 was transferred into a *Streptomyces lividans* TK23 strain (ε-poly-L-lysine non-producing actinomycete) in accordance with the method described in Reference Material (Practical *Streptomyces* Genetics (2000) P. 301-302). The resultant transformant was aerobically cultivated in an ε-poly-L-lysine production medium containing 650 µg/ml of neomycin at 30° C. for 30 hours (3 L Jar-fermentor).

After completion of the cultivation, purification of the recombinant Pls was carried out from 15 g (wet weight) of a bacterial cell recovered by centrifugation in a manner similar to Example 4 by using a chromatography resin for His-tag fused protein purification, Ni Sepharose 6 Fast Flow (made by GE Healthcare Corporation). When the crude extract was subjected to purification to clarify whether or not His-tag fused recombinant Pls was expressed, approximately 1 mg of recombinant Pls could be obtained similarly to the case where *S. albulus* was used as a host. Thus, the expression vector having the pls promoter fully functioned in an actinomycete other than *S. albulus* even in an ε-poly-L-lysine non-producing actinomycete, and could be utilized for producing a recombinant protein.

On the other hand, the amount of ε-poly-L-lysine accumulated in culture supernatant was very small with a productivity of 0.1 g/l after 30 hours cultivation when quantitatively measured by HPLC method described in JP 2008-263868 A. It was presumed that precursor (L-lysine or ATP) supply in *S. lividans* used as a host was insufficient. From the result described above, it was demonstrated that a more efficient production of useful substances by catalysis of a transgene product (enzyme protein or the like) is achievable by using an ε-poly-L-lysine producer (*S. albulus*, for example) as a host for producing arbitrary useful substances.

INDUSTRIAL APPLICABILITY

The invention is useful for producing desired useful substances.

The invention is also useful as a host-vector system which is to be a tool for linking gene information obtained by genomic analyses with production of useful substances, an enzyme catalyzing synthesis thereof, or the like.

What is claimed is:

1. An expression vector, comprising a promoter and a terminator downstream of the promoter, wherein said promoter comprises the nucleotide sequence of SEQ ID NO: 1, SEQ ID NO: 2, SEQ ID NO: 3 or SEQ ID NO: 4 and wherein the terminator comprises the nucleotide sequence of SEQ ID NO: 7 or SEQ ID NO: 8.

2. An ε-poly-L-lysine producer comprising an objective gene and the expression vector according to claim 1 capable of expressing the objective gene.

3. The ε-poly-L-lysine producer according to claim 2, wherein the ε-poly-L-lysine producer is the actinomycete, *Streptomyces* species, the actinomycete, *Kitasatospora* species, or the filamentous fungus, *Epichloe* species.

4. The ε-poly-L-lysine producer according to claim 3, wherein the actinomycete, *Streptomyces* species, is *S. albulus*.

5. The ε-poly-L-lysine producer according to claim 2, further comprising a tag sequence under regulation of the promoter.

6. The ε-poly-L-lysine producer according to claim 5, wherein the tag sequence comprises the nucleotide sequence of SEQ ID NO: 9 or SEQ ID NO: 10.

7. The ε-poly-L-lysine producer according to claim 2, comprising an objective gene under control of the promoter.

8. The ε-poly-L-lysine producer according to claim 7, wherein the objective gene is a gene or gene cluster derived from an organism of a kind identical with or different from the ε-poly-L-lysine producer.

9. The ε-poly-L-lysine producer according to claim 8, wherein the objective gene is a pls gene, a bpsA gene, a hasA gene, a mhasA gene, a hasB gene, a hasB homolog gene, a hasD gene or a hasD homolog gene.

10. An expression vector, comprising the nucleotide sequence of SEQ ID NO: 6, SEQ ID NO: 14 or SEQ ID NO: 15.

11. An isolated host cell, comprising the expression vector of claim 1.

12. The host cell according to claim 11, which is the actinomycete, *Streptomyces* species, the actinomycete, *Kitasatospora* species, or the filamentous fungus, *Epichloe* species.

13. The host cell according to claim 12, which is an ε-poly-L-lysine producer.

14. A method for producing useful substances, comprising cultivating the host cell according to claim 11.

* * * * *

SEQUENCE LISTING

<160> NUMBER OF SEQ ID NOS: 33

<210> SEQ ID NO 1
<211> LENGTH: 50
<212> TYPE: DNA
<213> ORGANISM: Streptomyces albulus

<400> SEQUENCE: 1
gaagtcgatg aatatgtgct cagttgcgca atcatttaga caaggcttga          50

<210> SEQ ID NO 2
<211> LENGTH: 50
<212> TYPE: DNA
<213> ORGANISM: Streptomyces albulus

<400> SEQUENCE: 2
ttttatcggc acgggggagt ggtgccgaaa acaatccccg gcccgagtca          50

<210> SEQ ID NO 3
<211> LENGTH: 50
<212> TYPE: DNA
<213> ORGANISM: Streptomyces albulus

<400> SEQUENCE: 3
gtggtgccga aaacaatccc cggcccgagt caattctttc ccacgccgtg          50

<210> SEQ ID NO 4
<211> LENGTH: 343
<212> TYPE: DNA
<213> ORGANISM: Streptomyces albulus

<400> SEQUENCE: 4
gaagtcgatg aatatgtgct cagttgcgca atcatttaga caaggcttga ccggttgacc      60
cgtgaccgat cgggatcacg gtcctgacct gcggttttat cggcacgggg gagtggtgcc     120
gaaaacaatc cccggcccga gtcaattctt tcccacgccg tggtcaggcg ccgcggccgc     180 tttccggcg ccgcctgccc aagcgcccga tggccgcttt cacagcacgt cgaattgcg     240 gaacagaccg cgcggcaggc gaacccgctg cctgagcagc gacatctcta ggggcgaacg     300
tccgagggtc atccacccac cggcaccgaa cagaggcata tcg                     343

<210> SEQ ID NO 5
<211> LENGTH: 71
<212> TYPE: DNA
<213> ORGANISM: Artificial Sequence
<220> FEATURE:
<223> OTHER INFORMATION: Term-F

<400> SEQUENCE: 5
ggcatgcaag cttgagcgct ccgcgtgccc ggtggcggac ggtaccccgt ccgccaccgg    60
gcacggccgg c                                                         71

<210> SEQ ID NO 6
<211> LENGTH: 79
<212> TYPE: DNA
<213> ORGANISM: Artificial Sequence
<220> FEATURE:
<223> OTHER INFORMATION: Term-R

<400> SEQUENCE: 6
agctgccggc cgtgcccggt ggcggacggg gtaccgtccg ccaccgggca cgcggagcgc    60
tcaagcttgc atgcctgca                                                 79

<210> SEQ ID NO 7
<211> LENGTH: 42
<212> TYPE: DNA
<213> ORGANISM: Artificial Sequence
<220> FEATURE:
<223> OTHER INFORMATION: Predicted Terminator region

<400> SEQUENCE: 7
cgtgcccggt ggcggacggt accccgtccg ccaccgggca cg                       42

<210> SEQ ID NO 8
<211> LENGTH: 42
<212> TYPE: DNA
<213> ORGANISM: Artificial Sequence
<220> FEATURE:
<223> OTHER INFORMATION: Predicted Terminator region

<400> SEQUENCE: 8
cgtgcccggt ggcggacggg gtaccgtccg ccaccgggca cg                       42

<210> SEQ ID NO 9
<211> LENGTH: 45
<212> TYPE: DNA
<213> ORGANISM: Artificial Sequence
<220> FEATURE:
<223> OTHER INFORMATION: His8C-F

<400> SEQUENCE: 9
ggcatgcaag cttcaccacc accaccacca ccaccactga tatcc                    45

<210> SEQ ID NO 10
<211> LENGTH: 53
<212> TYPE: DNA
<213> ORGANISM: Artificial Sequence
<220> FEATURE:
<223> OTHER INFORMATION: His8C-R

<400> SEQUENCE: 10
agctggatat cagtggtggt ggtggtggtg gtggtgaagc ttgcatgcct gca            53

<210> SEQ ID NO 11
<211> LENGTH: 24
<212> TYPE: DNA
<213> ORGANISM: Artificial Sequence
<220> FEATURE:
<223> OTHER INFORMATION: His x 8-tag region

<400> SEQUENCE: 11
caccaccacc accaccacca ccac                                           24

```
<210> SEQ ID NO 12
<211> LENGTH: 24
<212> TYPE: DNA
<213> ORGANISM: Artificial Sequence
<220> FEATURE:
<223> OTHER INFORMATION: His x 8-tag region

<400> SEQUENCE: 12
gtggtggtgg tggtggtggt ggtg                                              24

<210> SEQ ID NO 13
<211> LENGTH: 8217
<212> TYPE: DNA
<213> ORGANISM: Artificial Sequence
<220> FEATURE:
<223> OTHER INFORMATION: pLAK007

<400> SEQUENCE: 13
cgataagcta gcttcacgct gccgcaagca ctcagggcgc aagggctgct aaaggaagcg        60
gaacacgtag aaagccagtc gcagaaacg gtgctgaccc cggatgaatg tcagctactg       120
ggctatctgg acaagggaaa acgcaagcgc aaagagaaag caggtagctt gcagtgggct       180
tacatgcgaa tagctagact gggcggtttt atggacagca agcgaaccgg aattgccagc       240
tggggcgccc tctggtaagg ttgggaagcc ctgcaaagta aactggatgg ctttcttgcc       300
gccaaggatc tgatggcgca ggggatcaag atctgatcaa gagacaggat gaggatcgtt       360
tcgcatgatt gaacaagatg gattgcacgc aggttctccg gccgcttggg tggagaggct       420
attcggctat gactgggcac aacagacaat cggctgctct gatgccgccg tgttccggct       480
gtcagcgcag gggcgcccgg ttcttttttgt caagaccgac ctgtccggtg ccctgaatga      540
actccaagac gaggcagcgc ggctatcgtg gctggccacg acgggcgttc cttgcgcagc       600
tgtgctcgac gttgtcactg aagcgggaag ggactggctg ctattgggcg aagtgccggg       660
gcaggatctc ctgtcatctc accttgctcc tgccgagaaa gtatccatca tggctgatgc       720
aatgcggcgg ctgcatacgc ttgatccggc tacctgccca ttcgaccacc aagcgaaaca       780
tcgcatcgag cgagcacgta ctcggatgga agccggtctt gtcgatcagg atgatctgga       840
cgaagagcat caggggctcg cgccagccga actgttcgcc aggctcaagg cgcggatgcc       900
cgacggcgag gatctcgtcg tgacccatgg cgatgcctgc ttgccgaata tcatggtgga       960
aaatggccgc ttttctggat tcatcgactg tggccggctg ggtgtggcgg accgctatca      1020
ggacatagcg ttggctaccc gtgatattgc tgaagagctt ggcggcgaat gggctgaccg      1080
cttcctcgtg ctttacggta tcgccgctcc cgattcgcag cgcatcgcct tctatcgcct      1140
tcttgacgag ttcttctgag cgggactctg ggttcgaaa tgaccgacca agcgacgccc       1200
aacctgccat cacgagattt cgattccacc gccgccttct atgaaaggtt gggcttcgga      1260
atcgttttcc gggacgccct cgcggacgtg ctcatagtcc acgacgcccg tgattttgta      1320
gccctggccg acgccagca ggtaggccga caggctcatg ccggccgccg ccgccttttc       1380
ctcaatcgct cttcgttcgt ctggaaggca gtacaccttg ataggtgggc tgcccttcct      1440
ggttggcttg gtttcatcag ccatccgctt gccctcatct gttacgccgg cggtagccgg      1500
ccagcctcgc agagcaggat tcccgttgag caccgccagg tgcgaataag ggacagtgaa      1560
gaaggaacac ccgctcgcgg gtgggcctac ttcacctatc ctgccccgct gacgccgttg      1620
gatacaccaa ggaaagtcta cacgaaccct ttggcaaaat cctgtatatc gtgcgaaaaa      1680
ggatggatat accgaaaaaa tcgctataat gaccccgaag cagggttatg cagcggaaaa      1740
```

```
gcgctgcttc cctgctgttt tgtggaatat ctaccgactg gaaacaggca aatgcaggaa   1800
attactgaac tgaggggaca ggcgagagac gatgccaaag agctcctgaa aatctcgata   1860
actcaaaaaa tacgcccggt agtgatctta tttcattatg gtgaaagttg gaacctctta   1920
cgtgccgatc aacgtctcat tttcgccaaa agttggccca gggcttcccg gtatcaacag   1980
ggacaccagg atttatttat tctgcgaagt gatcttccgt cacaggtatt tattcggcgc   2040
aaagtgcgtc gggtgatgct gccaacttac tgatttagtg tatgatggtg ttttgaggt   2100 gctccagtgg cttctgtttc tatcagctcc tgaaaatctc gataactcaa aaatacgcc   2160 cggtagtgat cttatttcat tatggtgaaa gttggaacct cttacgtgcc gatcaacgtc   2220 tcatttcgc caaaagttgg cccagggctt cccggtatca acagggacac caggatttat   2280
ttattctgcg aagtgatctt ccgtcacagg tatttattcg gcgcaaagtg cgtcgggtga   2340
tgctgccaac ttactgattt agtgtatgat ggtgttttg aggtgctcca gtggcttctg   2400
tttctatcag gctggatga tcctccagcg cggggatctc atgctggagt tcttcgccca   2460
ccccaaaagg atctaggtga agatcctttt tgataatctc atgaccaaaa tcccttaacg   2520
tgagttttcg ttccactgag cgtcagaccc cgtagaaaag atcaaggat cttcttgaga   2580 tcctttttt ctgcgcgtaa tctgctgctt gcaaacaaaa aaaccaccgc taccagcggt   2640
ggtttgtttg ccggatcaag agctaccaac tcttttccg aaggtaactg gcttcagcag   2700
agcgcagata ccaaatactg tccttctagt gtagccgtag ttaggccacc acttcaagaa   2760
ctctgtagca ccgcctacat acctcgctct gctaatcctg ttaccagtgg ctgctgccag   2820
tggcgataag tcgtgtctta ccgggttgga ctcaagacga tagttaccgg ataaggcgca   2880
gcggtcgggc tgaacggggg gttcgtgcac acagcccagc ttggagcgaa cgacctacac   2940
cgaactgaga tacctacagc gtgagcattg agaaagcgcc acgcttcccg aagggagaaa   3000
ggcggacagg tatccggtaa gcggcagggt cggaacagga gagcgcacga gggagcttcc   3060
agggggaaac gcctggtatc tttatagtcc tgtcgggttt cgccacctct gacttgagcg   3120
tcgatttttg tgatgctcgt caggggggcg gagcctatgg aaaaacgcca gcaacgcggc   3180 cttttacgg ttcctggcct tttgctggcc ttttgctcac atgttctttc ctgcgttatc   3240
ccctgattct gtggataacc gtattaccgc ctttgagtga gctgataccg ctcgccgcag   3300
ccgaacgacc gagcgcagcg agtcagtgag cgaggaagcg gaagagcgcc caatacgcaa   3360
accgcctctc cccgcgcgtt ggccgattca ttaatgcagc tggcacgaca ggtttcccga   3420
ctggaaagcg ggcagtgagc gcaacgcaat taatgtgagt tagctcactc attaggcacc   3480
ccaggcttta cactttatgc ttccggctcg tatgttgtgt ggaattgtga gcggataaca   3540
atttcacaca ggaaacagct atgaccatga ttacgaattc gagctcggta cccggggatc   3600
accggcaccg gccgcagcgc ccggagcatc aagtgggtc acttcggtgc cgacatgtgg   3660
accctcaagg gcgccggccg ccgcaaggcc ccgagctgt tcgccggcgg cgagctgttg   3720
gcactcggcg gacgcaggac gatgcaaacg ctgctgcacg aggccgcaca cgccgtcgcg   3780
cacgtccggc ggatcgccga caccagcagc gatggccgct accacaacag gcgtttcgtg   3840 gccgtcgcg aggaactggg actcgccggc ccgccgcga gcgtcccagt caacggctgg   3900
aacgagtgca ccatcacgga tgccaccgcg gccaagtacg ccgccgccat cgaggccctg   3960
gaccaagccc aactccccta cctccacgac cccttgccc tcttgatcgg cggcgccgac   4020
cccggcaccg ccacggcagg cgaggacggc gaggacgagg acgaggacca ggacccgcag   4080
```

-continued

```
gagggccccg tcaggccgaa gaagaagcgg gggaacaccc gattcctcat cacctgccag  4140
tgcaccgagg agggcaaaga cggcgaactc cagcccgccc gccgcatcca gatcagccgc  4200
aaggcatgga tggccggcgg agaagacggc ggattgcact gccacgcatg cgcatccccc  4260
ttcaccccgg ccgagcccat cgaccctgac ggcgaagaag acgactagtc agcctcaggg  4320
gccagcacgg tgacaggcgt cgcgtcaagt cagaacgagt gcaatatccc ttaaggggct  4380
tttggcgggg gaactttcaa cacgccgagg gaaagtgcag caattctcct ccctggtgct  4440
gcacttttgt ggcatgatcc ttgaccatgg aaaaggatca gcaaccgcgg cgtcgcggga  4500
tgccgcgcgt tacccggtac cgtgctccgt cctacgaccc ggcgagcggt ggtccctacc  4560
gcccaggaac aggttttgag ccggacaacg ccatgaagct catcgacatg tgcgccgcgc  4620
tgaacatgtc cgtcgccggg ttcctcaacg ccctagtagg cgtggtggag gtagaccccc  4680
aaacgggtgg gcctatggga tggccgtccg cagcacagct caaggaggcc agttgaagga  4740
acgggcgcgc gtaagggcgc ttcggacttc ctaaccgaag cgcgtacgta agccccaggt  4800
cccccccgggt cccagcacct tcaggttccc caaccaccgc tgagactccg ggccccagaa  4860
aaagcacatc agccgccgtt tgtgccggtt tcctaggccg acgagcgggg gcgtctgtgc  4920
gtcctcttag caccgaggag ctgtcgccat cgtagcgcag agccacggtg gcggtacctc  4980
tttgcctcaa tccggggtgt ctgagggggcg atttgtcgac actgccaccg catcgcatcg  5040
agatgttttg tcccggtttc tccgggagtt gtcgccgagc cggaaggtgc ggcgagcgca  5100
gttcatcggc gacgacagtt cgcgtgtaca ggagaattcc gccactgttt gggctaactc  5160
gtatccggtt gtcatcgacc gggacagagg ggacgggtcg cgcgccggtcg cgatgtattt  5220
gaccggtttc cgcaaccgca agggtgggcg ccgcagcgac cgctaccacg tttacgtgta  5280
cgtcgtgttc gagctggacg tgtcgagggg cggacgggag cgcgtacgcc gtcacgccgc  5340
cgccctggtc gagttgctgg cagcgcacgg catcggcgcg gtgccggtca actccggtcc  5400
gagcgggggc atgcacgtgt gggtggcgtg tccgcagggc ttgccgccgg tggtggtggc  5460
ccggatcgcg gatgcggccc aggccctgtt cccgacggtg gaccgcacgc cgctgttgaa  5520
ccccgccagc ggagccgtca ggccccccgg cgctccgcac cgccacggcg ggtacgccga  5580
acttgtccgg cacagtgtcg aggaagcggt cgcggtcctc aagcagggtg cccaggcccg  5640
cgcgttcgtg gcgctgctgc gcgatctgga ggcccaggcg aaggcggccg gcttgtggcg  5700
cgtggcggat gcggcactcg gcgagtcccg ggcacgccgc ggtgggagcg gcggccggtc  5760
ggttccgccg tccatcgcgg cccgcggccc ggtggtgcgg ccggtcgtga ccgacgaggg  5820
cggtgtgccc cggctggacg tgccctggcg cctcctgagc ggcgccgccc gacgcggcgc  5880
cgagcaccgc cccagcagca ccccggcgc ccaccaggcg gccgtacacc ccgttttgcg  5940
gtccatggcc gccgccgggt ggcaccgcgg cgaggccgcc gcgttcgccg ccgacccga  6000
gttgtccccg gcgctggagt ggttgcgcac cgccagcacc gccaccggcg agcgtgcccc  6060
gctcaccgag gcggaggccg aggaccggct caccgcgcg tggtggctcg cggtgcagga  6120
cgccgcccgg atgccccacc gccgcgcgga gaccgaccag gacgacgagc agcaaggcgc  6180
cgccgagggc atggccgctg ccaccgacct gatcgcccgc atggaggcgt gcgggcacgc  6240
ccactggacc aggcccagcg gccccgccga ccgcgccgtg ttgcgcgcgc tcgcatggtt  6300
catggccgcc tacgggctgg tcgaggtgac cgccagcgtc cgccggatcg ccgtactcgc  6360
cggctactcc aagtccacgg ccgcactgtc cctgcaacgc gtcacctacg acgggtggat  6420
cgagaccgcg aaggacgccg agcgccgcac cagcagtggc cgccgcatcc ggctggcccg  6480
```

```
cgcccaccag tgcaccgccg acgagcacca catgtgcgcc cttcacgacc tgccagcaga    6540
cagcaaaaca gcaggtcacc acgggtcgga cagaagcgga acaccccgcc ccccagggg     6600 cggggtggga gtccttggcc gtctcggagg attggttgcc catcagcagg cgggtatctg    6660
gcaccggttc gggcaccacg cggcccgcac gctggagatc atcaaggacc acccggccgg    6720
cgtgagcccg gaggagatca cccagcacag cggctacacg gcccgtacga ccgcccggca    6780
ctgcggcagg ctggtggagg ccggcttggc ggagatcacc gctgagggcg ccctcgtgcc    6840
gacggaccgg agcctgtacg aggccggggc gcgcgtggga gtggccagcc gtcccgtgga    6900
actcgccgtg gtgccccgag tcgagcagag ccaacaccag tggtggtgcc gagaagaggc    6960
gtggtggcag ctcgaccgcg acgagcgccg aagccgaggc ccccgggcca gcgccgacca    7020
agcggttctc cccggcctgg acccgtacgc ccgcgcctac ccccgccagg cccccaccga    7080
gctgggacag cccggagccg ccgaccactc ccgcgcgttc gccatcgagg ccgcccggat    7140
cggcgccgcc gaactcgccg ccgaggccac caccccttgcg cagcgcggcg aggtcatcga    7200
ccccgcccga ctcgccggcc accggcccac cgcggcggag cccggcacga tcacgctcgc    7260
cgcctgagcg cgtggaggcc ccgcaggacg cgccgacaca cccaaagggt gaaccgcgcc    7320
acgggagggc acccgaggcg ctacagtagg caccacagga cggcgacaga tcaccacgga    7380
ctgagcaggc gagtccgagg agccgaccga aacccgcagc ggcgaacacc cgccggcgga    7440
gtgcaggccc cgcaccgcgt gatgtgtgta cacgcgaacg gccagcgtgc tgggcatagc    7500
ccgccgccga gaccggacgg gccaccgggc cgcagggacc gacgaagcac ccgcccgcg     7560 agcgggccga ccgaccggcc ggccgttggt cgacgtccgc gggcgtctcg gggtgtaccg    7620
gacgcacggc gagggtatgg ccgtgtcatg acaccgcgat gaggtcggcg tgagaagtcg    7680
atgaatatgt gctcagttgc gcaatcattt agacaaggct tgaccggttg acccgtgacc    7740
gatcgggatc acgtcctga cctgcggtttt tatcgcacg ggggagtggt gccgaaaaca     7800
atccccggcc cgagtcaatt ctttcccacg ccgtggtcag gcgccgcggc cgctttcccg    7860
gcgccgcctg cccaagcgcc cgatggccgc tttcacagca cgttcgaatt gcggaacaga    7920
ccgcgcggca ggcgaacccg ctgcctgagc agcgacatct ctaggggcga acgtccgagg    7980
gtcatccacc caccggcacc gaacagaggc atacatatgg gatcctctag agtcgacctg    8040
caggcatgca agcttggcac tggccgtcgt tttacaacgt cgtgactggg aaaaccctgg    8100
cgttacccaa cttaatcgcc ttgcagcaca tccccctttc gccagctggc gtaatagcga    8160
agaggcccgc accgatcgcc cttcccaaca gttgcgcagc ctgaatggcg aatggcg      8217
```

<210> SEQ ID NO 14
<211> LENGTH: 8280
<212> TYPE: DNA
<213> ORGANISM: Artificial Sequence
<220> FEATURE:
<223> OTHER INFORMATION: pLAK008

<400> SEQUENCE: 14

```
cgataagcta gcttcacgct gccgcaagca ctcagggcgc aagggctgct aaaggaagcg      60
gaacacgtag aaagccagtc cgcagaaacg gtgctgaccc cggatgaatg tcagctactg     120
ggctatctgg acaagggaaa acgcaagcgc aaagagaaag caggtagctt gcagtgggct     180
tacatggcga tagctagact gggcggtttt atggacagca agcgaaccgg aattgccagc     240
tggggcgccc tctggtaagg ttgggaagcc ctgcaaagta aactggatgg ctttcttgcc     300
```

```
gccaaggatc tgatggcgca ggggatcaag atctgatcaa gagacaggat gaggatcgtt    360
tcgcatgatt gaacaagatg gattgcacgc aggttctccg gccgcttggg tggagaggct    420
attcggctat gactgggcac aacagacaat cggctgctct gatgccgccg tgttccggct    480
gtcagcgcag gggcgccggg ttcttttttgt caagaccgac ctgtccggtg ccctgaatga   540
actccaagac gaggcagcgc ggctatcgtg gctggccacg acgggcgttc cttgcgcagc    600
tgtgctcgac gttgtcactg aagcgggaag ggactggctg ctattgggcg aagtgccggg    660
gcaggatctc ctgtcatctc accttgctcc tgccgagaaa gtatccatca tggctgatgc    720
aatgcggcgg ctgcatacgc ttgatccggc tacctgccca ttcgaccacc aagcgaaaca    780
tcgcatcgag cgagcacgta ctcggatgga agccggtctt gtcgatcagg atgatctgga    840
cgaagagcat caggggctcg cgccagccga actgttcgcc aggctcaagg cgcggatgcc    900
cgacggcgag gatctcgtcg tgacccatgg cgatgcctgc ttgccgaata tcatggtgga    960
aaatggccgc ttttctggat tcatcgactg tggccggctg ggtgtggcgg accgctatca   1020
ggacatagcg ttgctacccc gtgatattgc tgaagagctt ggcggcgaat gggctgaccg   1080
cttcctcgtg ctttacggta tcgccgctcc cgattcgcag cgcatcgcct tctatcgcct   1140
tcttgacgag ttcttctgag cgggactctg gggttcgaaa tgaccgacca agcgacgccc   1200
aacctgccat cacgagattt cgattccacc gccgccttct atgaaaggtt gggcttcgga   1260
atcgttttcc gggacgccct cgcggacgtg ctcatagtcc acgacgcccg tgattttgta   1320
gccctggccg acggccagca ggtaggccga caggctcatg ccggccgccg ccgccttttc   1380
ctcaatcgct cttcgttcgt ctggaaggca gtacaccttg ataggtgggc tgcccttcct   1440
ggttggcttg gtttcatcag ccatccgctt gccctcatct gttacgccgg cggtagccgg   1500
ccagcctcgc agagcaggat tcccgttgag caccgccagg tgcgaataag ggacagtgaa   1560
gaaggaacac ccgctcgcgg gtgggcctac ttcacctatc ctgccccgct gacgccgttg   1620
gatacaccaa ggaaagtcta cacgaaccct ttggcaaaat cctgtatatc gtgcgaaaaa   1680
ggatggatat accgaaaaaa tcgctataat gaccccgaag cagggttatg cagcggaaaa   1740
gcgctgcttc cctgctgttt tgtggaatat ctaccgactg gaaacaggca aatgcaggaa   1800
attactgaac tgagggggaca ggcgagagac gatgccaaag agctcctgaa aatctcgata   1860
actcaaaaaa tacgcccggt agtgatctta tttcattatg gtgaaagttg gaacctctta   1920
cgtgccgatc aacgtctcat tttcgccaaa agttggccca gggcttcccg gtatcaacag   1980
ggacaccagg atttatttat tctgcgaagt gatcttccgt cacaggtatt tattcggcgc   2040
aaagtgcgtc gggtgatgct gccaacttac tgatttagtg tatgatggtg tttttgaggt   2100
gctccagtgg cttctgtttc tatcagctcc tgaaaatctc gataactcaa aaaatacgcc   2160
cggtagtgat cttatttcat tatggtgaaa gttggaacct cttacgtgcc gatcaacgtc   2220
tcattttcgc caaagttggg cccagggctt cccggtatca acaggacaca caggatttat   2280
ttattctgcg aagtgatctt ccgtcacagg tatttattcg gcgcaaagtg cgtcgggtga   2340
tgctgccaac ttactgattt agtgtatgat ggtgttttttg aggtgctcca gtggcttctg   2400
tttctatcag ggctggatga tcctccacgc ggggatctc atgctggagt tcttcgccca   2460
ccccaaaagg atctaggtga agatcctttt tgataatctc atgaccaaaa tcccttaacg   2520
tgagttttcg ttccactgag cgtcagaccc cgtagaaaag atcaaaggat cttcttgaga   2580
tccttttttt ctgcgcgtaa tctgctgctt gcaaacaaaa aaaccaccgc taccagcggt   2640
ggtttgtttg ccggatcaag agctaccaac tcttttttccg aaggtaactg gcttcagcag   2700
```

```
agcgcagata ccaaatactg tccttctagt gtagccgtag ttaggccacc acttcaagaa    2760
ctctgtagca ccgcctacat acctcgctct gctaatcctg ttaccagtgg ctgctgccag    2820
tggcgataag tcgtgtctta ccgggttgga ctcaagacga tagttaccgg ataaggcgca    2880
gcggtcgggc tgaacggggg gttcgtgcac acagcccagc ttggagcgaa cgacctacac    2940
cgaactgaga tacctacagc gtgagcattg agaaagcgcc acgcttcccg aagggagaaa    3000
ggcggacagg tatccggtaa gcggcagggt cggaacagga gagcgcacga gggagcttcc    3060 aggggggaaac gcctggtatc tttatagtcc tgtcgggttt cgccacctct gacttgagcg    3120 tcgattttttg tgatgctcgt cagggggggcg gagcctatgg aaaaacgcca gcaacgcggc    3180 cttttttacgg ttcctggcct tttgctggcc ttttgctcac atgttctttc ctgcgttatc    3240
ccctgattct gtggataacc gtattaccgc ctttgagtga ctgataccg ctcgccgcag    3300 ccgaacgacc gagcgcagcg agtcagtgag cgaggaagcg gaagagcgcc caatacgcaa    3360
accgcctctc cccgcgcgtt ggccgattca ttaatgcagc tggcacgaca ggtttcccga    3420
ctggaaagcg ggcagtgagc gcaacgcaat taatgtgagt tagctcactc attaggcacc    3480
ccaggcttta cactttatgc ttccggctcg tatgttgtgt ggaattgtga gcggataaca    3540
atttcacaca ggaaacagct atgaccatga ttacgaattc gagctcggta cccggggatc    3600
accggcaccg gccgcagcgc ccggagcatc aagtggggtc acttcggtgc cgacatgtgg    3660
accctcaagg gcgccggccg ccgcaaggcc cccgagctgt tcgccggcgg cgagctgttg    3720
gcactcggcg gacgcaggac gatgcaaacg ctgctgcacg aggccgcaca cgccgtcgcg    3780
cacgtccggc ggatcgccga caccagcagc gatggccgct accacaacag gcgtttcgtg    3840
gccgtcgcgg aggaactggg actgccggcc ccgccgcga gcgtcccagt caacggctgg    3900
aacgagtgca ccatcacgga tgccaccgcg gccaagtacg ccgccgccat cgaggccctg    3960
gaccaagccc aactccccta cctccacgac ccccttgccc tcttgatcgg cggcgccgac    4020
cccggcaccg ccacggcagg cgaggacggc gaggacgagg acgaggacca ggacccgcag    4080
gagggccccg tcaggccgaa gaagaagcgg ggaacaccc gattcctcat cacctgccag    4140
tgcaccgagg agggcaaaga cggcgaactc cagcccgccc gccgcatcca gatcagccgc    4200
aaggcatgga tggccggcgg agaagacggc ggattgcact gccacgcatg cgcatccccc    4260
ttcacccccg ccgagcccat cgaccctgac ggcgaagaag acgactagtc agcctcaggg    4320
gccagcacgg tgacaggcgt cgcgtcaagt cagaacgagt gcaatatccc ttaaggggct    4380
tttggcgggg gaacttttcaa cacgccgagg gaaagtgcag caattctcct ccctggtgct    4440
gcacttttgt ggcatgatcc ttgaccatgg aaaaggatca gcaaccgcgg cgtcgcggga    4500
tgccgcgcgg tacccggtac cgtgctccgt cctacgaccc ggcgagcggt ggtccctacc    4560
gcccaggaac aggttttgag ccggacaacg ccatgaagct catcgacatg tgcgccgcgc    4620
tgaacatgtc cgtcgccggg ttcctcaacg ccctagtagg cgtggtggag gtagaccccc    4680
aaacgggtgg gcctatggga tggccgtccg cagcacagct caaggaggcc agttgaagga    4740
acgggcgcgc gtaagggcgc ttcggacttc ctaaccgaag cgcgtacgta agccccaggt    4800
ccccccgggt cccagcacct tcaggttccc caaccaccgc tgagactccg ggccccagaa    4860
aaagcacatc agccgccgtt tgtgccggtt tcctaggccg acgagcgggg gcgtctgtgc    4920
gtcctcttag caccgaggag ctgtcgccat cgtagcgcag agccacggtg gcggtacctc    4980
tttgcctcaa tccggggtgt ctgaggggcg atttgtcgac actgccaccg catcgcatcg    5040
```

```
agatgttttg tcccggtttc tccgggagtt gtcgccgagc cggaaggtgc ggcgagcgca    5100
gttcatcggc gacgcagtt cgcgtgtaca ggagaattcc gccactgttt gggctaactc     5160
gtatccggtt gtcatcgacc gggacgaggt ggacgggtcg gcgccggtcg cgatgtattt    5220
gaccggtttc cgcaaccgca agggtgggcg ccgcagcgac cgctaccacg tttacgtgta    5280
cgtcgtgttc gagctggacg tgtcgagggg cggacgggag gcggtacgcc gtcacgccgc    5340
cgccctggtc gagttgctgg cagcgcacgg catcggcgcg gtgccggtca actccggtcc    5400
gagcgggggc atgcacgtgt gggtggcgtg tccgcagggc ttgccgccgg tggtggtggc    5460
ccggatcgcg gatgcggccc aggccctgtt cccgacggtg gaccgcacgc cgctgttgaa    5520
ccccgccagc ggagccgtca ggccccccgg cgctccgcac cgccacggcg ggtacgccga    5580
acttgtccgg cacagtgtcg aggaagcggt cgcggtcctc aagcagggtg cccaggcccg    5640
cgcgttcgtg gcgctgctgc gcgatctgga ggcccaggcg aaggcggccg gcttgtggcg    5700
cgtggcggat gcggcactcg gcgagtcccg ggcacgccgc ggtgggagcg gcggccggtc    5760
ggttccgccg tccatcgcgg cccgcggccc ggtggtgcgg ccggtcgtga ccgacgaggg    5820
cggtgtgccc cggctggacg tgccctggcg cctcctgagc ggcgccgccc gacgcggcgc    5880
cgagcaccgc cccagcagca cccccggcgc ccaccaggcg gccgtacacc ccgttttgcg    5940
gtccatggcc gccgccgggt ggcaccgcgg cgaggccgcc gcgttcgccc cgaccccga    6000 gttgtccccg gcgctggagt ggttgcgcac cgccagcacc gccaccggcg agcgtgcccc    6060
gctcaccgag gcggaggccg aggaccggct cacccgcgcg tggtggctcg cggtgcagga    6120
cgccgcccgg atgccccacc gccgcgcgga gaccgaccag gacgacgagc agcaaggcgc    6180
cgccgagggc atggccgctg ccaccgacct gatcgcccgc atggaggcgt gcgggcacgc    6240
ccactggacc aggcccagcg gccccgccga ccgcgccgtg ttgcgcgcgc tcgcatggtt    6300
catggccgcc tacgggctgg tcgaggtgac cgccagcgtc cgccggatcg ccgtactcgc    6360
cggctactcc aagtccacgg ccgcactgtc cctgcaacgc gtcacctacg acgggtggat    6420
cgagaccgcg aaggacgccg agcgccgcac cagcagtggc cgccgcatcc ggctggcccg    6480
cgcccaccag tgcaccgccg acgagcacca catgtgcgcc cttcacgacc tgccagcaga    6540
cagcaaaaca gcaggtcacc acgggtcgga cagaagcgga acaccccgcc ccccagggg    6600 cggggtggga gtccttggcc gtctcggagg attggttgcc catcagcagg cgggtatctg    6660
gcaccggttc gggcaccacg cggcccgcac gctggagatc atcaaggacc acccggccgg    6720
cgtgagcccg gaggagatca cccagcacag cggctacacg gcccgtacga ccgcccggca    6780
ctgcggcagg ctggtggagg ccggcttggc ggagatcacc gctgagggcg ccctcgtgcc    6840 gacgaccgg agcctgtacg aggccggggc gcggtggga gtggccagcc gtcccgtgga    6900
actcgccgtg gtggcccgag tcgagcagag ccaacaccag tggtggtgcc gagaagaggc    6960
gtggtggcag ctcgaccgcg acgagcgccg aagccgaggc cccgggcca gcgccgacca    7020 agcggttctc cccggcctgg acccgtacgc ccgcgcctac ccccgccagg cccccaccga    7080
gctgggacag cccggagccg ccgaccactc ccgcgcgttc gccatcgagg ccgcccggat    7140
cggcgccgcc gaactcgccg ccgaggccac caccttgcg cagcgcggcg aggtcatcga    7200
ccccgcccga ctcgccggcc accggcccac cgcgcgcgga cccggcacga tcacgctcgc    7260
cgcctgaggc cgtggaggcc ccgcaggacg cgccgacaca cccaaagggt gaaccgcgcc    7320
acgggagggc acccgaggcg ctacagtagg caccacagga cggcgacaga tcaccacgga    7380
ctgagcaggc gagtccgagg agccgaccga aacccgcagc ggcgaacacc cgccggcgga    7440
```

```
gtgcaggccc cgcaccgcgt gatgtgtgta cacgcgaacg gccagcgtgc tgggcatagc   7500
ccgccgccga gaccggacgg gccaccgggc gcagggaccg acgaagcac ccgcccgcg    7560 agcgggccga ccgaccggcc ggccgttggt cgacgtccgc gggcgtctcg gggtgtaccg   7620
gacgcacggc gagggtatgg ccgtgtcatg acaccgcgat gaggtcggcg tgagaagtcg   7680
atgaatatgt gctcagttgc gcaatcattt agacaaggct tgaccggttg acccgtgacc   7740
gatcgggatc acggtcctga cctgcggttt tatcggcacg gggagtggt gccgaaaaca    7800 atccccggcc cgagtcaatt cttccccacg ccgtggtcag gcgccgcggc cgctttcccg   7860
gcgccgcctg cccaagcgcc cgatggccgc tttcacagca cgttcgaatt gcggaacaga   7920
ccgcgcggca ggcgaacccg ctgcctgagc agcgacatct ctaggggcga acgtccgagg   7980
gtcatccacc caccgcacc gaacagaggc atacatatgg gatcctctag agtcgacctg    8040
caggcatgca agcttgagcg ctccgcgtgc ccggtggcgg acggtacccc gtccgccacc   8100
gggcacggcc ggcagcttgg cactggccgt cgttttacaa cgtcgtgact gggaaaaccc   8160
tggcgttacc caacttaatc gccttgcagc acatccccct ttcgccagct ggcgtaatag   8220
cgaagaggcc cgcaccgatc gcccttccca acagttgcgc agcctgaatg gcgaatggcg   8280
```

<210> SEQ ID NO 15
<211> LENGTH: 8317
<212> TYPE: DNA
<213> ORGANISM: Artificial Sequence
<220> FEATURE:
<223> OTHER INFORMATION: pLAK009

<400> SEQUENCE: 15

```
cgataagcta gcttcacgct gccgcaagca ctcagggcgc aagggctgct aaaggaagcg     60
gaacacgtag aaagccagtc cgcagaaacg gtgctgaccc cggatgaatg tcagctactg    120
ggctatctgg acaagggaaa acgcaagcgc aaagagaaag caggtagctt gcagtgggct    180
tacatggcga tagctagact gggcggtttt atggacagca agcgaaccgg aattgccagc    240
tggggcgccc tctggtaagg ttgggaagcc ctgcaaagta aactggatgg ctttcttgcc    300
gccaaggatc tgatggcgca ggggatcaag atctgatcaa gagacaggat gaggatcgtt    360
tcgcatgatt gaacaagatg gattgcacgc aggttctccg gccgcttggg tggagaggct    420
attcggctat gactgggcac aacagacaat cggctgctct gatgccgccg tgttccggct    480
gtcagcgcag ggcgcccgg ttcttttttgt caagaccgac ctgtccggtg ccctgaatga    540
actccaagac gaggcagcgc ggctatcgtg gctggccacg acgggcgttc cttgcgcagc    600
tgtgctcgac gttgtcactg aagcgggaag ggactggctg ctattgggcg aagtgccggg    660
gcaggatctc ctgtcatctc accttgctcc tgccgagaaa gtatccatca tggctgatgc    720
aatgcggcgg ctgcatacgc ttgatccggc tacctgccca ttcgaccacc aagcgaaaca    780
tcgcatcgag cgagcacgta ctcggatgga agccggtctt gtcgatcagg atgatctgga    840
cgaagagcat caggggctcg cgccagccga actgttcgcc aggctcaagg cgcggatgcc    900
cgacggcgag gatctcgtcg tgacccatgg cgatgcctgc ttgccgaata tcatggtgga    960
aaatggccgc ttttctggat tcatcgactg tggccggctg ggtgtggcgg accgctatca    1020
ggacatagcg ttggctaccc gtgatattgc tgaagagctt ggcggcgaat gggctgaccg    1080
cttcctcgtg ctttacggta tcgccgctcc cgattcgcag cgcatcgcct tctatcgcct    1140
tcttgacgag ttcttctgag cgggactctg gggttcgaaa tgaccgacca agcgacgccc    1200
```

```
aacctgccat cacgagattt cgattccacc gccgccttct atgaaaggtt gggcttcgga    1260
atcgttttcc gggacgccct cgcggacgtg ctcatagtcc acgacgcccg tgattttgta    1320
gccctggccg acggccagca ggtaggccga caggctcatg ccggccgccg ccgccttttc    1380
ctcaatcgct cttcgttcgt ctggaaggca gtacaccttg ataggtgggc tgcccttcct    1440
ggttggcttg gtttcatcag ccatccgctt gccctcatct gttacgccgg cggtagccgg    1500
ccagcctcgc agagcaggat tcccgttgag caccgccagg tgcgaataag ggacagtgaa    1560
gaaggaacac ccgctcgcgg gtgggcctac ttcacctatc ctgccccgct gacgccgttg    1620
gatacaccaa ggaaagtcta cacgaaccct ttggcaaaat cctgtatatc gtgcgaaaaa    1680
ggatggatat accgaaaaaa tcgctataat gaccccgaag cagggttatg cagcggaaaa    1740
gcgctgcttc cctgctgttt tgtggaatat ctaccgactg gaaacaggca aatgcaggaa    1800
attactgaac tgaggggaca ggcgagagac gatgccaaag agctcctgaa aatctcgata    1860
actcaaaaaa tacgcccggt agtgatctta tttcattatg gtgaaagttg gaacctctta    1920
cgtgccgatc aacgtctcat tttcgccaaa agttggccca gggcttcccg gtatcaacag    1980
ggacaccagg atttatttat tctgcgaagt gatcttccgt cacaggtatt tattcggcgc    2040
aaagtgcgtc gggtgatgct gccaacttac tgatttagtg tatgatggtg ttttttgaggt   2100 gctccagtgg cttctgtttc tatcagctcc tgaaaatctc gataactcaa aaaatacgcc    2160
cggtagtgat cttatttcat tatggtgaaa gttggaacct cttacgtgcc gatcaacgtc    2220 tcatttttcgc caaaagttgg cccagggctt cccggtatca acagggacac caggatttat    2280
ttattctgcg aagtgatctt ccgtcacagg tatttattcg gcgcaaagtg cgtcgggtga    2340
tgctgccaac ttactgattt agtgtatgat ggtgttttttg aggtgctcca gtggcttctg    2400
tttctatcag gctgatga tcctccagcg cggggatctc atgctggagt tcttcgccca     2460
ccccaaaagg atctaggtga agatcctttt tgataatctc atgaccaaaa tcccttaacg    2520
tgagttttcg ttccactgag cgtcagaccc cgtagaaaag atcaaggat cttcttgaga    2580 tccttttttt ctgcgcgtaa tctgctgctt gcaaacaaaa aaaccaccgc taccagcggt    2640
ggtttgtttg ccggatcaag agctaccaac tctttttccg aaggtaactg gcttcagcag    2700
agcgcagata ccaaatactg tccttctagt gtagccgtag ttaggccacc acttcaagaa    2760
ctctgtagca ccgcctacat acctcgctct gctaatcctg ttaccagtgg ctgctgccag    2820
tggcgataag tcgtgtctta ccgggttgga ctcaagacga tagttaccgg ataaggcgca    2880
gcggtcgggc tgaacggggg gttcgtgcac acagcccagc ttggagcgaa cgacctacac    2940
cgaactgaga tacctacagc gtgagcattg agaaagcgcc acgcttcccg aagggagaaa    3000
ggcggacagg tatccggtaa gcggcagggt cggaacagga gagcgcacga gggagcttcc    3060
agggggaaac gcctggtatc tttatagtcc tgtcgggttt cgccacctct gacttgagcg    3120
tcgatttttg tgatgctcgt caggggggcg gagcctatgg aaaaacgcca gcaacgcggc    3180
ctttttacgg ttcctggcct tttgctgcc ttttgctcac atgttctttc ctgcgttatc     3240
ccctgattct gtggataacc gtattaccgc ctttgagtga gctgataccg ctcgccgcag    3300
ccgaacgacc gagcgcagcg agtcagtgag cgaggaagcg gaagagcgcc caatacgcaa    3360
accgcctctc cccgcgcgtt ggccgattca ttaatgcagc tggcacgaca ggtttcccga    3420
ctggaaagcg ggcagtgagc gcaacgcaat taatgtgagt tagctcactc attaggcacc    3480
ccaggcttta cactttatgc ttccggctcg tatgttgtgt ggaattgtga gcggataaca    3540
atttcacaca ggaaacagct atgaccatga ttacgaattc gagctcggta cccggggatc    3600
```

```
accggcaccg gccgcagcgc ccggagcatc aagtggggtc acttcggtgc cgacatgtgg    3660
accctcaagg gcgccggccg ccgcaaggcc cccgagctgt tcgccggcgg cgagctgttg    3720
gcactcggcg gacgcaggac gatgcaaacg ctgctgcacg aggccgcaca cgccgtcgcg    3780
cacgtccggc ggatcgccga caccagcagc gatggccgct accacaacag gcgtttcgtg    3840
gccgtcgcgg aggaactggg actcgccggc cccgccgcga gcgtcccagt caacggctgg    3900
aacgagtgca ccatcacgga tgccaccgcg gccaagtacg ccgccgccat cgaggccctg    3960
gaccaagccc aactccccta cctccacgac ccccttgccc tcttgatcgg cggcgccgac    4020
cccggcaccg ccacggcagg cgaggacggc gaggacgagg acgaggacca ggacccgcag    4080
gagggccccg tcaggccgaa gaagaagcgg gggaacaccc gattcctcat cacctgccag    4140
tgcaccgagg agggcaaaga cggcgaactc cagcccgccc gccgcatcca gatcagccgc    4200
aaggcatgga tggccggcgg agaagacggc ggattgcact gccacgcatg cgcatccccc    4260 ttcaccccg cccgagcccat cgaccctgac ggcgaagaag acgactagtc agcctcaggg    4320
gccagcacgg tgacaggcgt cgcgtcaagt cagaacgagt gcaatatccc ttaaggggct    4380
tttggcgggg aacttttcaa cacgccgagg gaaagtgcag caattctcct ccctggtgct    4440
gcacttttgt ggcatgatcc ttgaccatgg aaaaggatca gcaaccgcgg cgtcgcggga    4500 tgccgcgcg tacccggtac cgtgctccgt cctacgaccc ggcgagcggt ggtccctacc    4560
gcccaggaac aggttttgag ccggacaacg ccatgaagct catcgacatg tgcgccgcgc    4620
tgaacatgtc cgtcgccggg ttcctcaacg ccctagtagg cgtggtggag gtagacccc    4680 aaacgggtgg gcctatggga tggccgtccg cagcacagct caaggaggcc agttgaagga    4740
acgggcgcgc gtaagggcgc ttcggacttc ctaaccgaag cgcgtacgta agccccaggt    4800
ccccccgggt cccagcacct tcaggttccc caaccaccgc tgagactccg ggccccagaa    4860
aaagcacatc agccgccgtt tgtgccggtt cctaggccg acgagcgggg gcgtctgtgc    4920
gtcctcttag caccgaggag ctgtcgccat cgtagcgcag agccacggtg gcggtacctc    4980
tttgcctcaa tccggggtgt ctgagggggcg atttgtcgac actgccaccg catcgcatcg    5040
agatgttttg tccggtttc tccgggagtt gtcgccgagc cggaaggtgc ggcgagcgca    5100
gttcatcggc gacgcagtt cgcgtgtaca ggagaattcc gccactgttt gggctaactc    5160
gtatccggtt gtcatcgacc gggacgaggt ggacgggtcg cgccggtcg cgatgtattt    5220 gaccggtttc cgcaaccgca agggtgggcg ccgcagcgac cgctaccacg tttacgtgta    5280
cgtcgtgttc gagctggacg tgtcgagggg cggacgggag gcgtacgcc gtcacgccgc    5340 cgccctggtc gagttgctgg cagcgcacgg catcggcgcg gtgccggtca actccggtcc    5400 gagcggggc atgcacgtgt gggtggcgtg tccgcagggc ttgccgccgg tggtggtggc    5460
ccggatcgcg gatgcggccc aggccctgtt cccgacggtg gaccgcacgc cgctgttgaa    5520
ccccgccagc ggagccgtca ggccccccgg cgctccgcac cgccacggcg ggtacgccga    5580
acttgtccgg cacagtgtcg aggaagcggt cgcggtcctc aagcagggtg cccaggcccg    5640
cgcgttcgtg gcgctgctgc gcgatctgga ggcccaggcg aaggcggccg gcttgtggcg    5700
cgtggcggat gcggcactcg gcgagtcccg ggcacgccgc ggtgggagcg gcggccggtc    5760
ggttccgccg tccatcgcgg cccgcggccc ggtggtgcgg ccggtcgtga ccgacgaggg    5820
cggtgtgccc cggctggacg tgccctggcc cctcctgagc ggcgccgccc gacgcggcgc    5880
cgagcaccgc cccagcagca cccccggcgc ccaccaggcg gccgtacacc ccgttttgcg    5940
```

```
gtccatggcc gccgccgggt ggcaccgcgg cgaggccgcc gcgttcgccg ccgaccccga    6000
gttgtccccg gcgctggagt ggttgcgcac cgccagcacc gccaccggcg agcgtgcccc    6060
gctcaccgag gcggaggccg aggaccggct cacccgcgcg tggtggctcg cggtgcagga    6120
cgccgcccgg atgccccacc gccgcgcgga gaccgaccag gacgacgagc agcaaggcgc    6180
cgccgagggc atggccgctg ccaccgacct gatcgcccgc atggaggcgt gcgggcacgc    6240
ccactggacc aggcccagcg gccccgccga ccgcgccgtg ttgcgcgcgc tcgcatggtt    6300
catggccgcc tacgggctgg tcgaggtgac cgccagcgtc cgccggatcg ccgtactcgc    6360
cggctactcc aagtccacgg ccgcactgtc cctgcaacgc gtcacctacg acgggtggat    6420
cgagaccgcg aaggacgccg agcgccgcac cagcagtggc cgccgcatcc ggctggcccg    6480
cgcccaccag tgcaccgccg acgagcacca catgtgcgcc cttcacgacc tgccagcaga    6540
cagcaaaaca gcaggtcacc acgggtcgga cagaagcgga acaccccgcc ccccaggggg    6600
cggggtggga gtccttggcc gtctcggagg attggttgcc catcagcagg cgggtatctg    6660
gcaccggttc gggcaccacg cggcccgcac gctggagatc atcaaggacc acccggccgg    6720
cgtgagcccg gaggagatca cccagcacag cggctacacg gcccgtacga ccgcccggca    6780
ctgcggcagg ctggtggagg ccggcttggc ggagatcacc gctgagggcg ccctcgtgcc    6840
gacggaccgg agcctgtacg aggccggggc cgcggtggga gtggccagcc gtcccgtgga    6900
actcgccgtg gtgccccgag tcgagcagag ccaacaccag tggtggtgcc gagaagaggc    6960
gtggtggcag ctcgaccgcg acgagcgccg aagccgaggc ccccgggcca gcgccgacca    7020
agcggttctc cccggcctgg acccgtacgc ccgcgcctac ccccgccagg cccccaccga    7080
gctgggacag cccggagccg ccgaccactc ccgcgcgttc gccatcgagg ccgcccggat    7140
cggcgccgcc gaactcgccg ccgaggccac caccccttgcg cagcgcggcg aggtcatcga    7200
ccccgcccga ctcgccggcc accggcccac cgcggcggag cccggcacga tcacgctcgc    7260
cgcctgagcc cgtggaggcc ccgcaggacg cgccgacaca cccaaagggt gaaccgcgcc    7320
acgggagggc acccgaggcg ctacagtagg caccacagga cggcgacaga tcaccacgga    7380
ctgagcaggc gagtccgagg agccgaccga aacccgcagc ggcgaacacc cgccggcgga    7440
gtgcaggccc cgcaccgcgt gatgtgtgta cacgcgaacg gccagcgtgc tgggcatagc    7500
ccgccgccga gaccggacgg gccaccgggc cgcagggacc gacgaagcac ccgccccgcg    7560
agcgggccga ccgaccggcc ggccgttggt cgacgtccgc gggcgtctcg gggtgtaccg    7620
gacgcacggc gagggtatgg ccgtgtcatg acaccgcgat gaggtcggcg tgagaagtcg    7680
atgaatatgt gctcagttgc gcaatcattt agacaaggct tgaccggttg acccgtgacc    7740
gatcgggatc acggtcctga cctgcggttt tatcggcacg ggggagtggt gccgaaaaca    7800
atccccggcc cgagtcaatt ctttcccacg ccgtggtcag gcgccgcggc cgctttcccg    7860
gcgccgcctg cccaagcgcc cgatggccgc tttcacagca cgttcgaatt gcggaacaga    7920
ccgcgcggca ggcgaacccg ctgcctgagc agcgacatct ctaggggcga acgtccgagg    7980
gtcatccacc caccggcacc gaacagaggc atacatatgg gatcctctag agtcgacctg    8040
caggcatgca agcttcacca ccaccaccac caccaccact gatatccagc ttgagcgctc    8100
cgcgtgcccg gtggcggacg gtaccccgtc cgccaccggg cacggccggc agcttggcac    8160
tggccgtcgt tttacaacgt cgtgactggg aaaaccctgg cgttacccaa cttaatcgcc    8220
ttgcagcaca tccccctttc gccagctggc gtaatagcga agaggcccgc accgatcgcc    8280
cttcccaaca gttgcgcagc ctgaatggcg aatggcg                              8317
```

<210> SEQ ID NO 16
<211> LENGTH: 30
<212> TYPE: DNA
<213> ORGANISM: Artificial Sequence
<220> FEATURE:
<223> OTHER INFORMATION: e-PL-NRPS-F

<400> SEQUENCE: 16 ggggatcct cgtcgcccct tctcgaatcg                                30

<210> SEQ ID NO 17
<211> LENGTH: 30
<212> TYPE: DNA
<213> ORGANISM: Artificial Sequence
<220> FEATURE:
<223> OTHER INFORMATION: e-PL-NRPS-R

<400> SEQUENCE: 17
accaagcttt cacgcggccg cacctccctc                                30

<210> SEQ ID NO 18
<211> LENGTH: 30
<212> TYPE: DNA
<213> ORGANISM: Artificial Sequence
<220> FEATURE:
<223> OTHER INFORMATION: Ask-C4

<400> SEQUENCE: 18
accaagcttt catcgcccgg tgccgccgta                                30

<210> SEQ ID NO 19
<211> LENGTH: 30
<212> TYPE: DNA
<213> ORGANISM: Artificial Sequence
<220> FEATURE:
<223> OTHER INFORMATION: Ask-N4

<400> SEQUENCE: 19 ggggatccg gccttgtcgt gcagaagtac                                30

<210> SEQ ID NO 20
<211> LENGTH: 27
<212> TYPE: DNA
<213> ORGANISM: Artificial Sequence
<220> FEATURE:
<223> OTHER INFORMATION: eplP-F

<400> SEQUENCE: 20
actatggccg gccgttggtc gacgtcc                                27

<210> SEQ ID NO 21
<211> LENGTH: 35
<212> TYPE: DNA
<213> ORGANISM: Artificial Sequence
<220> FEATURE:
<223> OTHER INFORMATION: eplP-R

<400> SEQUENCE: 21
aggaaggatc ccatatgtat gcctctgttc ggtgc                                35

<210> SEQ ID NO 22
<211> LENGTH: 29
<212> TYPE: DNA
<213> ORGANISM: Artificial Sequence
<220> FEATURE:

<223> OTHER INFORMATION: plsnde-F

<400> SEQUENCE: 22
ggaattccat atgtcgtcgc cccttctcg                                  29

<210> SEQ ID NO 23
<211> LENGTH: 28
<212> TYPE: DNA
<213> ORGANISM: Artificial Sequence
<220> FEATURE:
<223> OTHER INFORMATION: plshind-R

<400> SEQUENCE: 23
acccaagctt tcacgcggcc gcacctcc                                   28

<210> SEQ ID NO 24
<211> LENGTH: 29
<212> TYPE: DNA
<213> ORGANISM: Artificial Sequence
<220> FEATURE:
<223> OTHER INFORMATION: plsnde-F

<400> SEQUENCE: 24
ggaattccat atgtcgtcgc cccttctcg                                  29

<210> SEQ ID NO 25
<211> LENGTH: 26
<212> TYPE: DNA
<213> ORGANISM: Artificial Sequence
<220> FEATURE:
<223> OTHER INFORMATION: plshindhis8-R

<400> SEQUENCE: 25
gtggtgaagc ttcgcggccg cacctc                                     26

<210> SEQ ID NO 26
<211> LENGTH: 40
<212> TYPE: DNA
<213> ORGANISM: Artificial Sequence
<220> FEATURE:
<223> OTHER INFORMATION: bpsAnde-F

<400> SEQUENCE: 26
ggaattccat atgactcttc aggagaccag cgtgctcgag                      40

<210> SEQ ID NO 27
<211> LENGTH: 34
<212> TYPE: DNA
<213> ORGANISM: Artificial Sequence
<220> FEATURE:
<223> OTHER INFORMATION: bpsAhind-R

<400> SEQUENCE: 27
cccaagcttc tcgccgagca ggtagcggat gtgc                            34

<210> SEQ ID NO 28
<211> LENGTH: 1298
<212> TYPE: DNA
<213> ORGANISM: Artificial Sequence
<220> FEATURE:
<223> OTHER INFORMATION: mhasA

<400> SEQUENCE: 28
gctctagaat gcgctcgcgc cgctggagcg ccgccaacct catcacggtc gtggccttca    60
gcatcttctg ggtcctgctc atctacgtca acgtgtacct gttcggcgcg cgcggctccc   120

| | |
|---|---|
| tcagcatcta cggcttcctg ctcatcgcct acctcctggt caagatgtcc ctcagcttct | 180 |
| tctacaagcc gttccgcggc cgggcgggcc agtacaaggt ggccgcgatc atcccgtcct | 240 |
| acaacgagga cgccgagtcg ctcctggaga ccctcaagag cgtccagcaa cagacgtacc | 300 |
| cgctggcaga gatctacgtg gtcgacacgg ggtccgccga cgagaccggc atcaagcgca | 360 |
| tcgaagacta cgtgcgggac acgggcgacc tcagctcgaa cgtcatcgtg caccgcagcg | 420 |
| agaagaacca gggcaagcgg cacgcccagg cctgggcgtt cgagcgctcc gacgccgacg | 480 |
| tcttcctgac ggtggacagc gacacctaca tctaccccga cgccctcgag gagctgctga | 540 |
| agacgttcaa cgacccgacc gtcttcgcgg ccacggggca cctgaacgtg cggaaccgcc | 600 |
| agacgaacct cctgacccgg ctcacggaca tccgctacga caacgccttc ggcgtcgaac | 660 |
| gggcggccca gtccgtcacc ggcaacatcc tggtgtgcag cgggcccctc tcggtctacc | 720 |
| gccgcgaggt ggtcgtgccg aacatcgatc ggtacatcaa ccagacgttc ctcggcatcc | 780 |
| cggtcagcat cggcgacgac cgctgcctga ccaactacgc gacggacctc ggcaagaccg | 840 |
| tgtaccagtc cacggccaag tgcatcaccg acgtcccgga caagatgagc acgtacctca | 900 |
| agcagcagaa ccggtggaac aagtccttct tccgcgagag catcatcagc gtccgccgga | 960 |
| tcatgaacaa cccgttcgtg gccctgtgga ccatcctcga agtctccatg ttcatgatgc | 1020 |
| tggtgtacag cgtcgtggac ttcttcgtcg gcaacgtgcg ggagttcgac tggctccgcg | 1080 |
| tcctggcgtt cctggtgatc atcttcatcg tcgcactctg ccggaacatc cactacatgc | 1140 |
| tgaagcaccc cctctccttc ctgctcagcc ccttctacgg cgtgctgcac ctcttcgtcc | 1200 |
| tgcaaccgct ccggctgtac tcgctcttca cgatccgcaa cgcggattgg ggcacccgga | 1260 |
| aggaggtcct cgcatgagcc tcaagatcac cgtgatcg | 1298 |

```
<210> SEQ ID NO 29
<211> LENGTH: 37
<212> TYPE: DNA
<213> ORGANISM: Artificial Sequence
<220> FEATURE:
<223> OTHER INFORMATION: sav5025-assembleF

<400> SEQUENCE: 29
ctcgcatgag cctcaagatc accgtgatcg gcaccgg                    37

<210> SEQ ID NO 30
<211> LENGTH: 45
<212> TYPE: DNA
<213> ORGANISM: Artificial Sequence
<220> FEATURE:
<223> OTHER INFORMATION: sav5025-assembleR

<400> SEQUENCE: 30
atggcgctca tgcggtggcc tcccccatcg cgcggtacgt ccagc            45

<210> SEQ ID NO 31
<211> LENGTH: 45
<212> TYPE: DNA
<213> ORGANISM: Artificial Sequence
<220> FEATURE:
<223> OTHER INFORMATION: sav3561-assembleF

<400> SEQUENCE: 31
cgatggggga ggccaccgca tgagcgccat ccgcccggca gccgt            45

<210> SEQ ID NO 32
```

<211> LENGTH: 37
<212> TYPE: DNA
<213> ORGANISM: Artificial Sequence
<220> FEATURE:
<223> OTHER INFORMATION: sav3561-hindR

<400> SEQUENCE: 32

| cccaagcttt cagtcttcgc cttccggctt ccgggaa | 37 |
|---|---|

<210> SEQ ID NO 33
<211> LENGTH: 4071
<212> TYPE: DNA
<213> ORGANISM: Artificial Sequence
<220> FEATURE:
<223> OTHER INFORMATION: mhasA-sav5025-sav3561

<400> SEQUENCE: 33

| gctctagaat gcgctcgcgc cgctggagcg ccgccaacct catcacggtc gtggccttca | 60 |
|---|---|
| gcatcttctg gtcctgctc atctacgtca acgtgtacct gttcggcgcg cgcggctccc | 120 |
| tcagcatcta cggcttcctg ctcatcgcct acctcctggt caagatgtcc ctcagcttct | 180 |
| tctacaagcc gttccgcggc cgggcgggcc agtacaaggt ggccgcgatc atcccgtcct | 240 |
| acaacgagga cgccgagtcg ctcctggaga ccctcaagag cgtccagcaa cagacgtacc | 300 |
| cgctggcaga gatctacgtg tcgacgacg gtccgccga cgagaccggc atcaagcgca | 360 |
| tcgaagacta cgtgcgggac acgggcgacc tcagctcgaa cgtcatcgtg caccgcagcg | 420 |
| agaagaacca gggcaagcgg cacgcccagg cctgggcgtt cgagcgctcc gacgccgacg | 480 |
| tcttcctgac ggtggacagc gacacctaca tctaccccga cgcctcgag gagctgctga | 540 |
| agacgttcaa cgacccgacc gtcttcgcgg ccacggggca cctgaacgtg cggaaccgcc | 600 |
| agacgaacct cctgacccgg ctcacggaca tccgctacga caacgccttc ggcgtcgaac | 660 |
| gggcggccca gtccgtcacc ggcaacatcc tggtgtgcag cgggccctc tcggtctacc | 720 |
| gccgcgaggt ggtcgtgccg aacatcgatc ggtacatcaa ccagacgttc ctcggcatcc | 780 |
| cggtcagcat cggcgacgac cgctgcctga ccaactacgc gacggacctc ggcaagaccg | 840 |
| tgtaccagtc cacggccaag tgcatcaccg acgtcccgga caagatgagc acgtacctca | 900 |
| agcagcagaa ccggtggaac aagtccttct tccgcgagag catcatcagc gtccgccgga | 960 |
| tcatgaacaa cccgttcgtg gccctgtgga ccatcctcga agtctccatg ttcatgatgc | 1020 |
| tggtgtacag cgtcgtggac ttcttcgtcg gcaacgtgcg ggagttcgac tggctccgcg | 1080 |
| tcctggcgtt cctggtgatc atcttcatcg tcgcactctg ccggaacatc cactacatgc | 1140 |
| tgaagcaccc cctctccttc ctgctcagcc ccttctacgg cgtgctgcac ctcttcgtcc | 1200 |
| tgcaaccgct ccggctgtac tcgctcttca cgatccgcaa cgcggattgg ggcacccgga | 1260 |
| aggaggtcct cgcatgagcc tcaagatcac cgtgatcggc accggctatc tcggcgccac | 1320 |
| acacgccgcg gccatggccg agctcggttt cgaggtgctc ggtctcgacg tcgtgcccga | 1380 |
| gaagatcgag atgctccagc ggggcgaggt cccgatgtac gagcccggtc tcgaggagct | 1440 |
| gctgcgcaag cacgtcgccg ggatcgaggg gtccaccggg cggctgcgct tcaccatgga | 1500 |
| cttcgccgag gtcgcggagt tcggcgacgt ccacttcgtc tgtgtgaaca cgccgcagaa | 1560 |
| gcacggtgag tacgcgtgcg acatgtcgta cgtcgacagc gccttcgagg cactcgcccc | 1620 |
| gcatctgaag gccccgccc tcgtcgtcgg caagtccacc gtgcccgtcg gctcggcgga | 1680 |
| ccggctcgcg gccggctcg cggagctggc gcccgcggt gaggacgccg agctcgcctg | 1740 |
| gaaccccgag ttcctgcgcg agggcttcgc cgtccaggac accctgcacc ccgaccggat | 1800 |

```
cgtcgtcggc gtgcgcagcg agcgcgccga gaagctgctg cgtgaggtgt acacgactcc    1860
ggtcgccgag ggctcgccct tcgtggtgac cgacttcccg accgccgagc tggtgaagac    1920
ctccgccaac tccttcctcg ccaccaagat ctccttcatc aacgcgatgg ccgaggtctg    1980
cgaggccgcg ggcggcgatg tcgtccagct ggccgaggcg ctcggtcacg acgaccggat    2040
cggcaagaag ttcctgcggg ccgggatcgg cttcggtggc gggtgcctgc caaggacat    2100
ccgtgccttc atggcgcgcg ccggcgagct gggcgccgac caggcgctga ccttcctgcg    2160
cgagatcgac tcgatcaaca tgcgccgccg tggccagatg gtcgagatgg cgcgcgaggc    2220
gctcggtggc ggatcgtttc tggggaagcg ggtcgccgtc ctcggtgcca ccttcaagcc    2280
cgactccgac gacgtacgcg actcgcccgc gctgaacgtc gccgggcaga tccacctcca    2340
gggcggccag gtcacggtgt acgacccgaa gggcatggac aacgcccggc ggctgttccc    2400
gacgctcggc tacgccgact cggcggtcgg ggccgtgcgg ggcgccgatg tcgtactgca    2460
cctgaccgag tggcgcgagt tccgtgagct ggacccggcg ccctcggcg aggccgcctc     2520
ggcccgcgtc ctgctcgacg ggcgcaacgc cctcgacccg cagctgtggc gccgggcggg    2580
ctggacgtac cgcgcgatgg gggaggccac cgcatgagcg ccatccgccc ggcagccgtc    2640
gtcgttctcg cagcgggtga gggcacccgt atgaagtcgg ccacacccaa ggtcctccac    2700
gacatctgcg ccgctccct cgtcggtcat gtactcgccg ccgcgcgcga gttggagccc     2760
gagaacctgg tcgtcgtcgt gggacacgcc cgtgagcagg tcaccgcgca cctcgccgag    2820
atcgacccgg ccgtgcgtac ggccgtccag gccgagcaga acgggaccgg gcacgccgtc    2880
cggatgggcc tcgaagagct cggcggcgtc gtcgacggga ccgtggtcgt cgtctgcggc    2940
gacacccccc tgctcagcgg ggagacgctg cggcagctcg ccgccacgca caccgccgac    3000
ggcaacgccg tcaccgtgct gaccgccgag gtccccgacg ccaccggcta cggccgcatc    3060
gtgcgcgacg gcgcctccgg tgccgtgacg gccatcgtcg agcacaagga cgccagcgag    3120
tcgcagcgcg ccgtccgtga gatcaactcc ggggtcttcg ccttcgacgg gcggctcctc    3180
gccgacgcgc tcggcaaggt gcgtaccgac aacagccagg gcgaggagta cctcaccgac    3240
gtcctcggga tcctgcgcga ggccgggcac cgggtgggcg cctccgtggc cgccgaccac    3300
cgggagatcg ccggcatcaa caaccgcgtg cagctggcgg aggcccgccg catcctcaac    3360
gaccggctcc tcacccgggc catgctcgcc ggcgtgacgg tggtggaccc ggcgaccacg    3420
tggatcgacg tgacggtcac cttcgggcag gacgcgatcg tgcacccggg gacgcagctc    3480
cagggcacca cgcagctggg tgagggtgcc gaggtcggcc ccaactcgcg gctcaaggac    3540
acccgggtcg gcgcgggcgc gcggatcgac aacacggtgg ccgagagggc ggacgtgggg    3600
gcgcaggcca gcgtcggtcc gttcgcgtat ctgcgtcccg gtacgcggct cggggcgaag    3660
gccaaggtgg gcacgtacgt cgagaccaag aacgcctcga tcggcgaggg cacgaaggtg    3720
ccgcacctgt cgtacgtggg tgacgcgacg atcggcgagt actccaacat cggtgccgcg    3780
agcgtgttcg tgaactacga cggtcaggac aagcaccaca ccacggtggg gtcgcactgc    3840
cgcaccggtt cggacaacat gtttgtggct cctgtcacgg tcggggacgg cgcgtacacc    3900
gcggcgggct cggtcatcac gaaggacgtg ccgcccggtt cgctggccgt ggcccgtggc    3960
cagcagcgga atatcgaggg ctgggtggcc cgtaagcgtc cgggaagtgc tgccgcgaag    4020
gcggccgagg tggcttcccg gaagccggaa ggcgaagact gaaagcttgg g             4071
```